(12) United States Patent
Shiina et al.

(10) Patent No.: US 10,696,703 B2
(45) Date of Patent: Jun. 30, 2020

(54) METHOD FOR PRODUCING EUSHEARLILIDES

(71) Applicant: TOKYO UNIVERSITY OF SCIENCE FOUNDATION, Shinjuku-Ku, Tokyo (JP)

(72) Inventors: Isamu Shiina, Tokyo (JP); Takayuki Tonoi, Tokyo (JP)

(73) Assignee: TOKYO UNIVERSITY OF SCIENCE FOUNDATION, Tokyo (JP)

( * ) Notice: Subject to any disclaimer, the term of this patent is extended or adjusted under 35 U.S.C. 154(b) by 554 days.

(21) Appl. No.: 15/519,279

(22) PCT Filed: Oct. 28, 2015

(86) PCT No.: PCT/JP2015/080469
§ 371 (c)(1),
(2) Date: Apr. 14, 2017

(87) PCT Pub. No.: WO2016/068220
PCT Pub. Date: May 6, 2016

(65) Prior Publication Data
US 2019/0382425 A1   Dec. 19, 2019

(30) Foreign Application Priority Data
Oct. 29, 2014   (JP) ................... 2014-220491

(51) Int. Cl.
*C07F 9/655*   (2006.01)
(52) U.S. Cl.
CPC .................... *C07F 9/655* (2013.01)

(58) Field of Classification Search
CPC ........ C07F 9/655; Y02P 20/55; C07D 313/00; A61K 31/685
USPC ....................................................... 549/222
See application file for complete search history.

(56) References Cited

U.S. PATENT DOCUMENTS

| | | | |
|---|---|---|---|
| 4,469,682 | A | 9/1984 | Mrozik |
| 4,918,098 | A | 4/1990 | Ramsay et al. |
| 2005/0215513 | A1 | 9/2005 | Boojamra et al. |

FOREIGN PATENT DOCUMENTS

| | | |
|---|---|---|
| JP | S59141582 A | 8/1984 |
| JP | S62265290 A | 11/1987 |
| JP | 2007536194 A | 12/2007 |

OTHER PUBLICATIONS

Hosoe, Tomoo et al., "A New Antifungal Macrolide, Eushearilide, Isolated from Eupenicillium shearii", Journal of Antibiotics, 2006, 59(9), p. 597-600.
International Search Report corresponding to Application No. PCT/JP2015/080469; dated Jan. 26, 2016, with English translation.
Yamauchi, Takayasu et al., "Total synthesis of the proposed structures of eushearilide", Heterocycles, 2014, vol. 88 (2), p. 1175-1189.

*Primary Examiner* — Taylor V Oh
(74) *Attorney, Agent, or Firm* — Cantor Colburn LLP

(57) ABSTRACT

Provided are: eushearilides; a method for producing eushearilides; a production intermediate; and a pharmaceutical composition containing eushearilides. By having the Wittig reaction process, Mukaiyama Aldol reaction process and Macrolactonizaion process serve as key processes, eushearilides represented by formula (I) are efficiently produced.

7 Claims, No Drawings

METHOD FOR PRODUCING EUSHEARLILIDES

This is the U.S. national stage of application No. PCT/JP2015/080469, filed Oct. 28, 2015. Priority under 35 U.S.C. § 119(a) and 35 U.S.C. § 365(b) is claimed from Japanese Application No. 2014-220491, filed Oct. 29, 2014, the disclosure of which is also incorporated herein by reference.

TECHNICAL FIELD

The present invention relates to eushearilides, a method of manufacturing the eushearilides, intermediates for manufacturing the eushearilides, and pharmaceutical compositions including the eushearilides.

BACKGROUND ART

Eushearilide is a natural macrolide, which was isolated in 2006 from one of the species of blue mold, *Eupenicillium shearii* IMF54447, has promising potential for application in the field of medicine (Nonpatent Document 1).

To date, the structure of eushearilide has been disclosed putatively in the above Nonpatent Document 1. The above document discloses that eushearilide has a 24-membered ring macrolide which has olefin portions at two positions and asymmetric carbon atoms at two positions, and also have a characteristic structure not seen in other macrolide compounds. However, the exact three dimensional structure thereof is yet to be elucidated.

An example of the total synthesis of a eushearilide analog is known (Nonpatent Document 2). Nonetheless, an efficient and large-scale method of manufacturing eushearilide and a derivative thereof is further demanded for physiological studies. Moreover, there have been demands for providing various eushearilide derivatives to facilitate medicine research in which eushearilide is used as a lead compound.

Non-Patent Document 1: T. Hosoe, K. Fukushima, K. Takizawa, T. Itabashi, N. Kawahara, V. Vidotto, K. Kawai, The Journal of Antibiotics, 2006, vol. 59, 597-600.

Non-Patent Document 2: T. Yamauchi, J. Takidaira, K. Okamoto, T. Sugiura, H. Horikoshi, S. Kudo, S. Sasaki, N. Mizushima, K. Higashiyama, Heterocycles, 2014, vol. 88, 1175-1189.

DISCLOSURE OF THE INVENTION

Problems to be Solved by the Invention

An object of the present invention is to solve the aforementioned problems in the conventional art. That is, an object of the present invention is to provide a method of manufacturing eushearilide and a derivative thereof, in which stereochemistry thereof can be controlled, and a large-scale and efficient supply thereof can be achieved. Another object of the present invention is to provide a novel and useful intermediate which enables efficient manufacture of various eushearilide derivatives.

Still another object of the present invention is to provide a novel eushearilide derivative and a pharmaceutical composition including the eushearilide derivative. Yet another object of the present invention is to provide an antimicrobial agent, in particular, an antimicrobial agent for resistant bacterium including the above eushearilide derivative.

Means for Solving the Problems

After conducting extensive studies, the present investors find that eushearilides can be efficiently manufactured via those key steps of the Wittig reaction step, the Mukaiyama aldol reaction step, the macrolactonization step, and the like. Then, the present invention has been completed.

Further, the present investors find that several novel eushearilides obtainable by the presently disclosed manufacturing method have an excellent antimicrobial activity, in particular, an antimicrobial activity against resistant bacteria such as methicillin-resistant *Staphylococcus aureus* (MRSA) and vancomycin-resistant *Enterococcus* (VRE). Then, the present invention has been completed.

That is, the present invention can provide the followings.

1) A method of manufacturing eushearilides represented by the formula (I), including the following steps 1 to 10, Step 1: a step of coupling a compound represented by the formula (I-1):

wherein P1 represents a protecting group, with a compound represented by the formula (I-2):

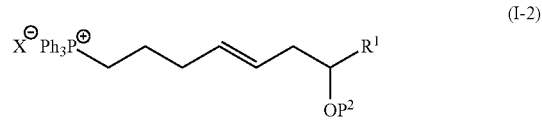

wherein R1 represents a hydrogen atom or an optionally substituted hydrocarbon group, and P2 represents a protecting group, and X represents a halogen atom, in the presence of a base to obtain a compound represented by the formula (I-3):

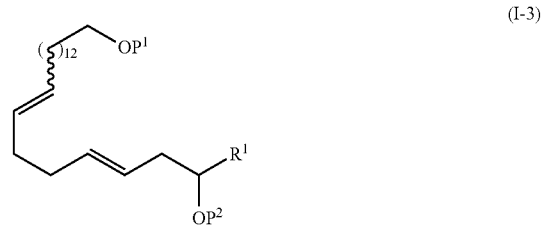

wherein R1, P1, and P2 are as defined above;

Step 2: a step of deprotecting the compound represented by the formula (I-3) to obtain a compound represented by the formula (I-4):

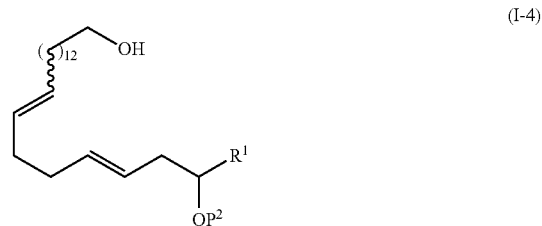

wherein R1 and P2 are as defined above;

Step 3: a step of oxidizing the compound represented by the formula (I-4) to obtain a compound represented by the formula (I-5):

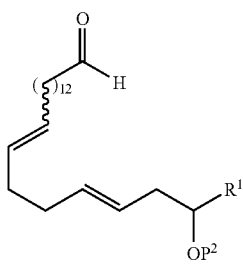
(I-5)

wherein R1 and P2 are as defined above;

Step 4: a step of subjecting the compound represented by the formula (I-5) to the aldol reaction to obtain a compound represented by the formula (I-6):

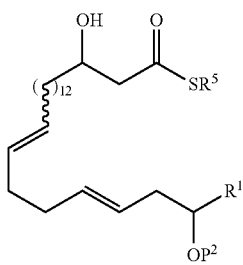
(I-6)

wherein R5 represents a hydrocarbon group, and R1 and P2 are as defined above;

Step 5: a step of transesterifying the compound represented by the formula (I-6) to obtain a compound represented by the formula (I-7):

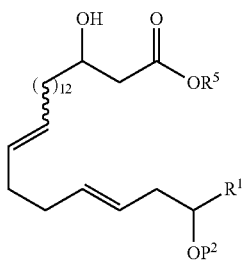
(I-7)

wherein R1, R5, and P2 are as defined above;

Step 6: a step of protecting, deprotecting the compound represented by the formula (I-7) to obtain a compound represented by the formula (I-8):

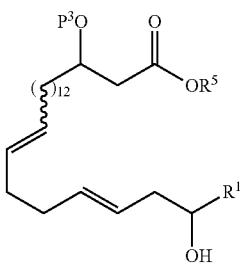
(I-8)

wherein P3 represents a protecting group, and R1 and R5 are as defined above;

Step 7: a step of hydrolyzing the compound represented by the formula (I-8) to obtain a compound represented by the formula (I-9):

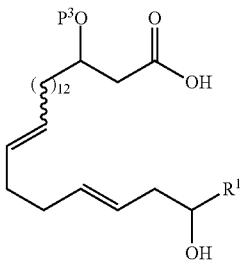
(I-9)

wherein R1 and P3 are as defined above;

Step 8: a step of cyclizing the compound represented by the formula (I-9) to obtain a compound represented by the formula (I-10):

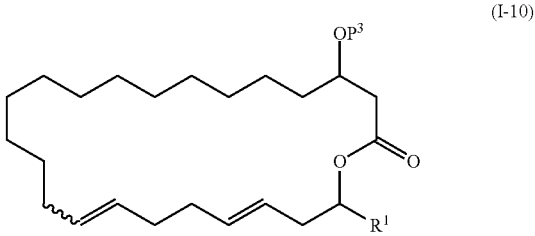
(I-10)

wherein R1 and P3 are as defined above;

Step 9: a step of deprotecting the compound represented by the formula (I-10) to obtain a compound represented by the formula (I-11):

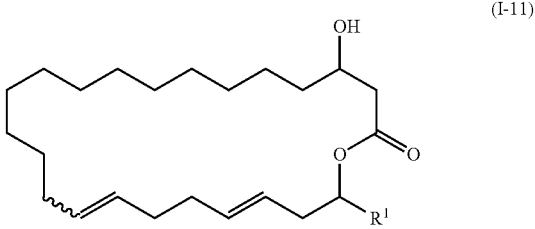
(I-11)

wherein R1 is as defined above;

Step 10: a step of allowing the compound represented by the formula (I-11) to react with a phosphorus compound, and then with an amine R2R3R4N to obtain the compound represented by the formula (I):

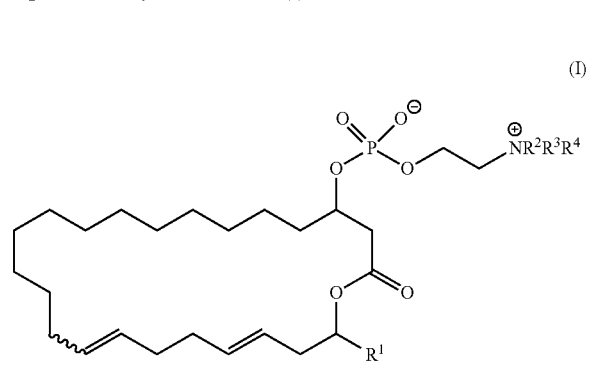

(I)

wherein R1 is as defined above, and R2, R3, and R4 independently represent a hydrogen atom or an optionally substituted hydrocarbon group.

(2) A method of manufacturing eushearilides represented by the formula (Ia), including allowing an compound represented by the formula (Ia-11):

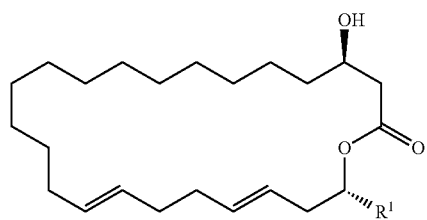

(Ia-11)

wherein R1 represents a hydrogen atom or an optionally substituted hydrocarbon group, to react with a phosphorus compound, and then with an amine R2R3R4N to obtain the eushearilide compound represented by the formula (Ia):

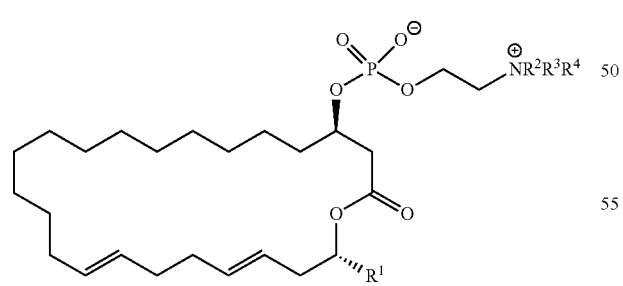

(Ia)

wherein R1, R2, R3, and R4 independently represent a hydrogen atom or an optionally substituted hydrocarbon group.

(3) The method according to the above (2), wherein the compound represented by the formula (Ia-11) is obtained by: a step of allowing a compound represented by the formula (Ia-9):

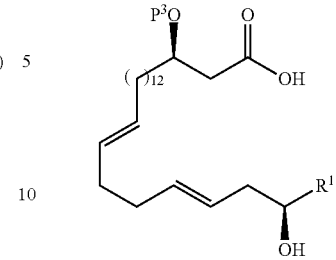

(Ia-9)

wherein R1 is as defined above, and P3 represents a protecting group, to react with 2-methyl-6-nitrobenzoic anhydride to obtain a compound represented by the formula (Ia-10):

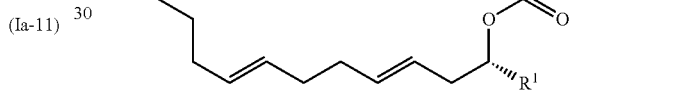

(Ia-10)

wherein R1 and P3 are as defined above, and a step of deprotecting the compound represented by the formula (Ia-10).

(4) The method according to the above (3), wherein the compound represented by the formula (Ia-9) is obtained by: a step of coupling the compound represented by the formula (I-1):

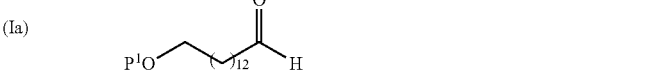

(I-1)

wherein P1 represents a protecting group, with a compound represented by the formula (Ia-2):

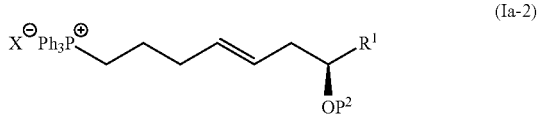

(Ia-2)

wherein R1 represents a hydrogen atom or an optionally substituted hydrocarbon group, and P2 represents a protecting group, and X represents a halogen atom, in the presence of a base to obtain a compound represented by the formula (Ia-3):

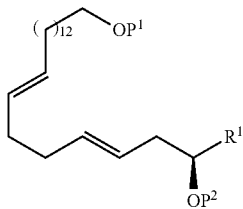

wherein R1, P1, and P2 are as defined above;
a step of deprotecting the compound represented by the formula (Ia-3) to obtain a compound represented by the formula (Ia-4):

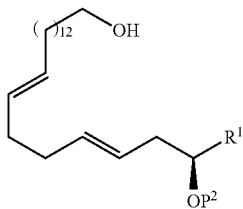

wherein R1 and P2 are as defined above;
a step of oxidizing the compound represented by the formula (Ia-4) to obtain a compound represented by the formula (Ia-5):

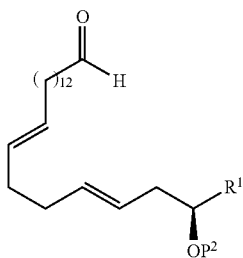

wherein R1 and P2 are as defined above;
a step of subjecting the compound represented by the formula (Ia-5) to the aldol reaction to obtain a compound represented by the formula (Ia-6):

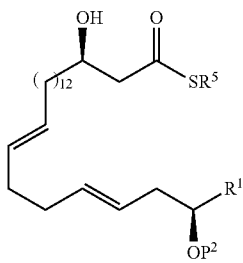

wherein R5 represents a hydrocarbon group, and R1 and P2 are as defined above;
a step of transesterifying the compound represented by the formula (Ia-6) to obtain a compound represented by the formula (Ia-7):

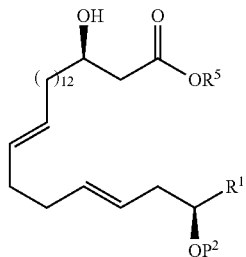

wherein R1, R5, and P2 are as defined above;
a step of protecting, deprotecting the compound represented by the formula (Ia-7) to obtain a compound represented by the formula (Ia-8):

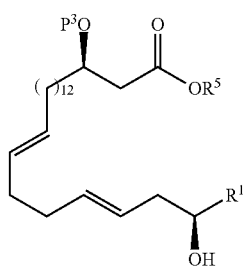

wherein P3 represents a protecting group, and R1 and R5 are as defined above; and a step of hydrolyzing the compound represented by the formula (Ia-8).

(5) The method according to any one of the above (2) to (4), wherein the eushearilides represented by the formula (Ia) is a compound represented by the formula (A):

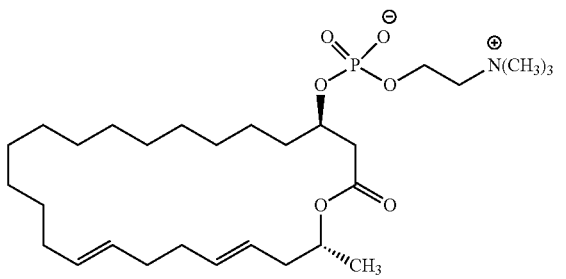

(6) A compound represented by the formula (II):

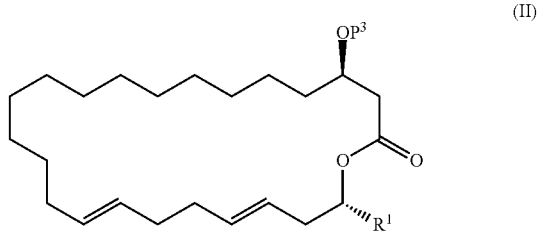

wherein R1 represents a hydrogen atom or an optionally substituted hydrocarbon group, and P3 represents a hydrogen atom or a protecting group, provided that a compound in the formula (II) in which R1 represents a methyl group, and P3 is a hydrogen atom or a benzyl group is excluded.

(7) A compound represented by the formula (A), (E), (F), or (G):

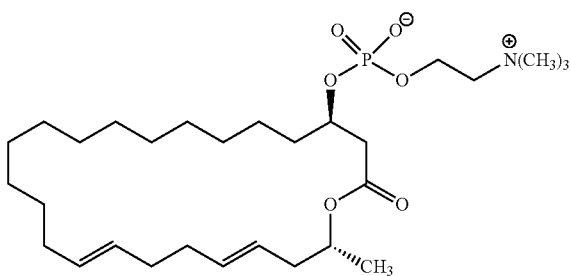

(A)

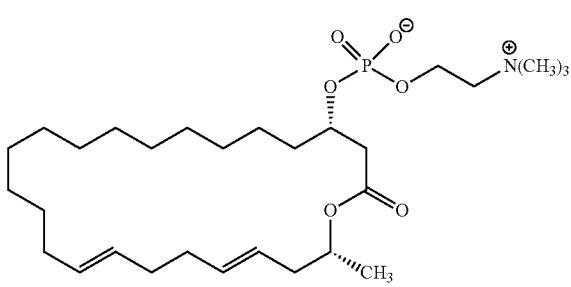

(E)

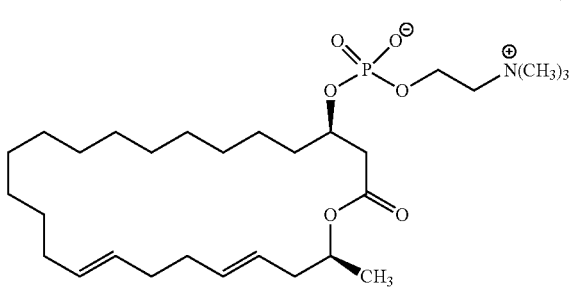

(F)

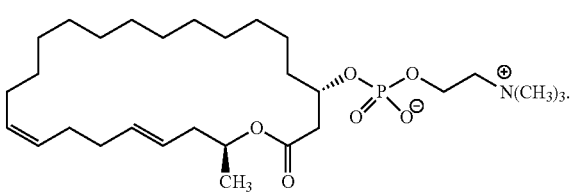

(G)

(8) A pharmaceutical composition including a compound represented by the formula (I):

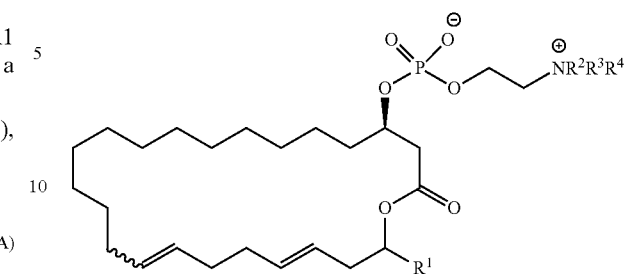

(I)

wherein R1, R2, R3, and R4 independently represent a hydrogen atom or an optionally substituted hydrocarbon group, provided that a compound (D):

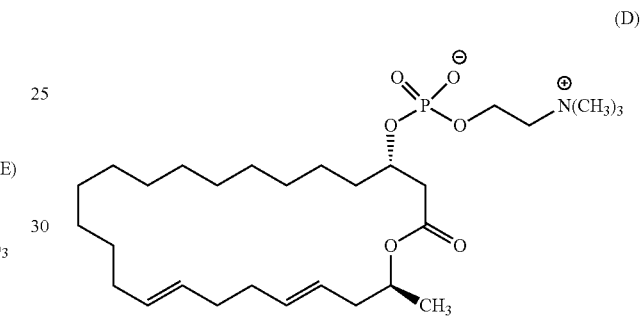

(D)

is excluded.

(9) The pharmaceutical composition according to the above (8), wherein the pharmaceutical composition is an antimicrobial agent.

(10) The pharmaceutical composition according to the above (9) or (10), wherein the compound represented by the formula (I) is a compound represented by the formula (A), (B), (C), (E), (F), (G), or (H):

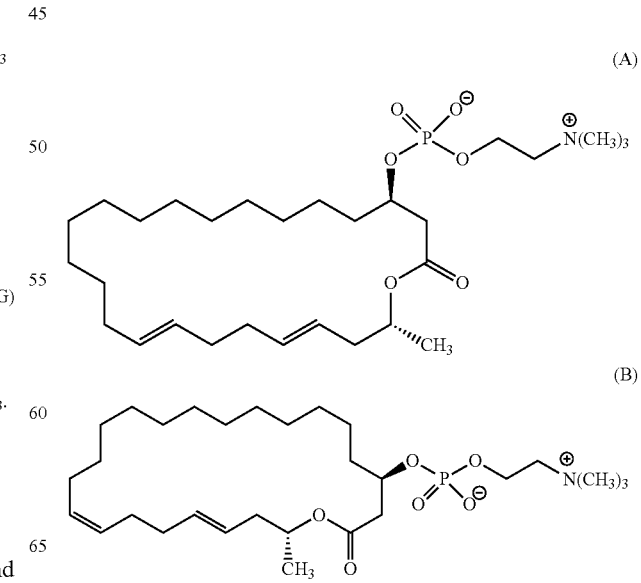

(A)

(B)

-continued

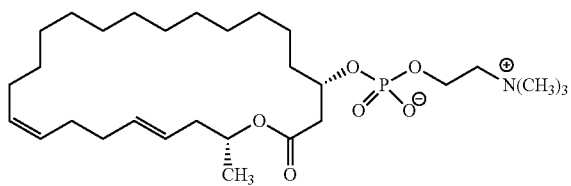
(C)

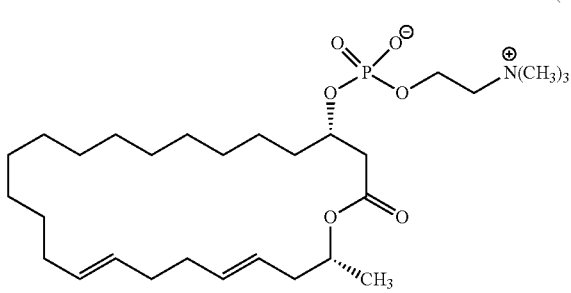
(E)

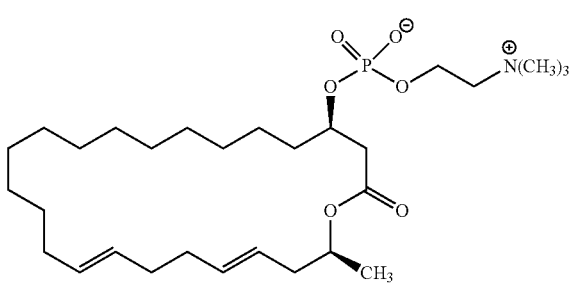
(F)

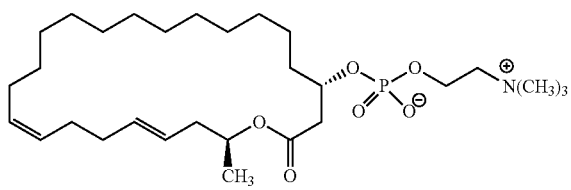
(G)

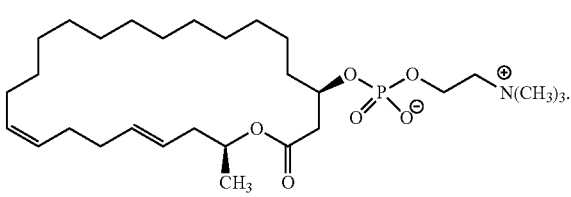
(H)

(11) An antimicrobial agent for resistant bacterium, including a compound represented by the formula (I):

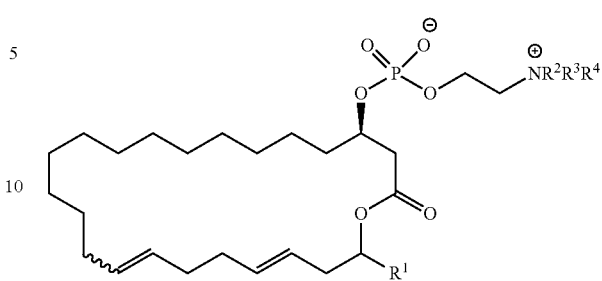
(I)

wherein R1, R2, R3, and R4 independently represent a hydrogen atom or an optionally substituted hydrocarbon group.

(12) The antimicrobial agent for resistant bacterium according to the above (11), wherein the compound represented by the formula (I) is a compound represented by the formula (A), (B), (C), (D), (E), (F), (G), or (H):

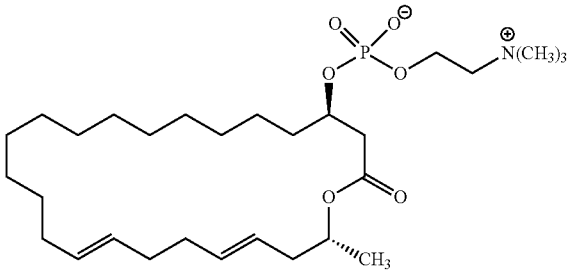
(A)

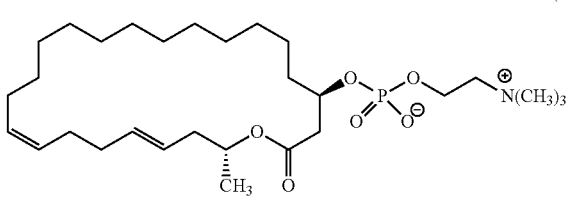
(B)

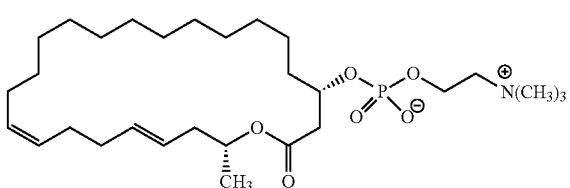
(C)

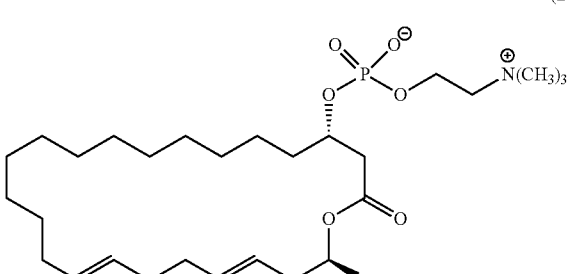
(D)

13
-continued

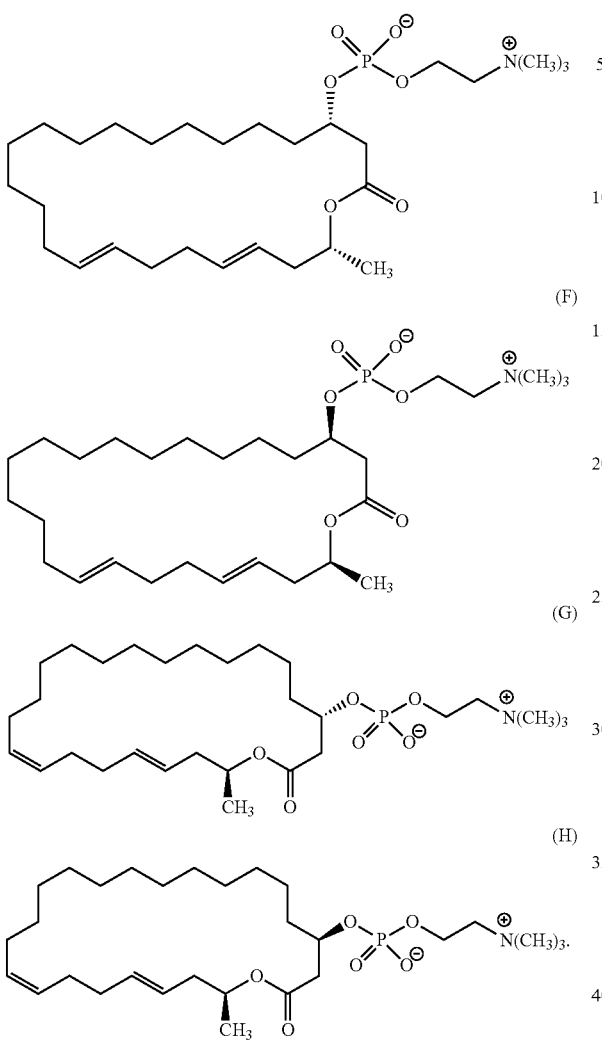

(13) The antimicrobial agent for resistant bacterium according to the above (11) or (12), wherein the resistant bacterium is methicillin-resistant *Staphylococcus aureus* (MRSA), vancomycin-resistant *Enterococcus* (VRE), or vancomycin-resistant *Staphylococcus aureus* (VRSA).

(14) A method of treating or preventing an resistant bacterial infection, including: administrating a therapeutically effective amount of a pharmaceutical composition including a compound represented by the formula (I):

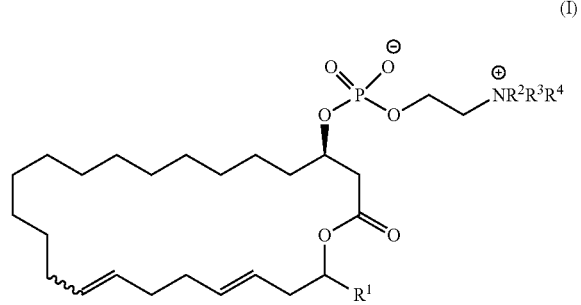

(I)

14 wherein R1, R2, R3, and R4 independently represent a hydrogen atom or an optionally substituted hydrocarbon group, to a subject in need thereof.

(15) Use of a compound represented by the formula (I):

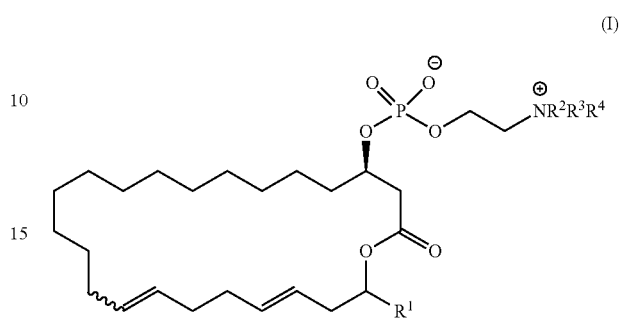

(I)

wherein R1, R2, R3, and R4 independently represent a hydrogen atom or an optionally substituted hydrocarbon group, for manufacturing an antimicrobial agent for resistant bacterium.

Effects of the Invention

The present invention can provide a method of manufacturing eushearilides in which the stereochemistry thereof can be controlled, and a large-scale and efficient supply thereof can be achieved. Further, the present invention can provide a novel and useful intermediate which enables efficient manufacture of various eushearilides.

Moreover, the present invention can provide pharmaceutical compositions including some of the eushearilides obtainable by the manufacturing method described above. Furthermore, the present invention can provide antimicrobial agents, in particular, antimicrobial agents for resistant bacteria including the above optically active eushearilides.

PREFERRED MODE FOR CARRYING OUT THE INVENTION

Eushearilides are 24-membered ring macrolides, and have a general backbone structure represented by the following formula.

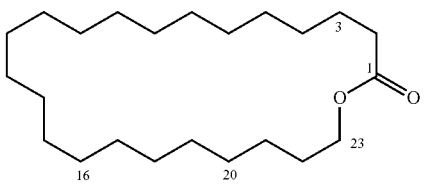

The numbers in the above formula represent positions of atoms in the general backbone structure.

Below, embodiments of the present invention will be described in detail.

The term "protecting group" as used in the present invention refers to a hydroxy protecting group in general. Hydroxy protecting groups include any groups which can be used as a common hydroxy protecting group, including, for example, those described in W. Greene et al., "Protective Groups in Organic Synthesis," 3rd Ed., p 17-245, 1999, John Wiley & Sons, INC. Protecting groups include, for example, acyl groups, alkyloxycarbonyl groups, aralkyloxycarbonyl groups, heterocyclic oxycarbonyl groups, alkyl groups, alkenyl groups, aralkyl groups, oxygen-containing heterocyclic groups, sulfur-containing heterocyclic groups, alkoxyalkyl groups, aralkyloxyalkyl groups, alkanesulfonyl groups, arylsulfonyl groups, substituted silyl groups, and the like. Specific examples of the protecting group include organosilicon-based protecting groups such as a tert-dimethylsilyl group, aralkyl groups such as a benzyl group and a 4-methoxybenzyl group, alkoxyalkyl groups such as a butoxymethyl group, a tetrahydropyran-2-yl group, and the like.

The term "hydrocarbon group" as used in the present invention means an alkyl group, an alkenyl group, an alkynyl group, and an aryl group. Examples of the "alkyl group" include linear, branched, or cyclic alkyl groups having 1 to 8 carbon atoms, for example, a methyl group, an ethyl group, a propyl group, an isopropyl group, and a cyclopropyl group. Examples of the "alkenyl group" and the "alkynyl group" include linear, branched, or cyclic alkenyl groups and alkynyl groups having 2 to 8 carbon atoms, for example, an ethenyl group, an ethynyl group, a propenyl group, a propynyl group, and a cyclohexenyl group. Examples of the "aryl group" include aryl groups having 6 to 18 carbon atoms, for example, a phenyl group, a naphthyl group, and an anthracenyl group.

Examples of the substituent of the "optionally substituted" as used in the present invention include, for example, a hydroxy group, an alkoxycarbonyl group, an amino group, an alkylamino group, an arylamino group, a nitro group, a cyano group, an alkoxy group, a carboxy group, a phosphate group, and the like.

Below, each of the steps in the manufacturing method according to the present invention will be described with reference to the following scheme.

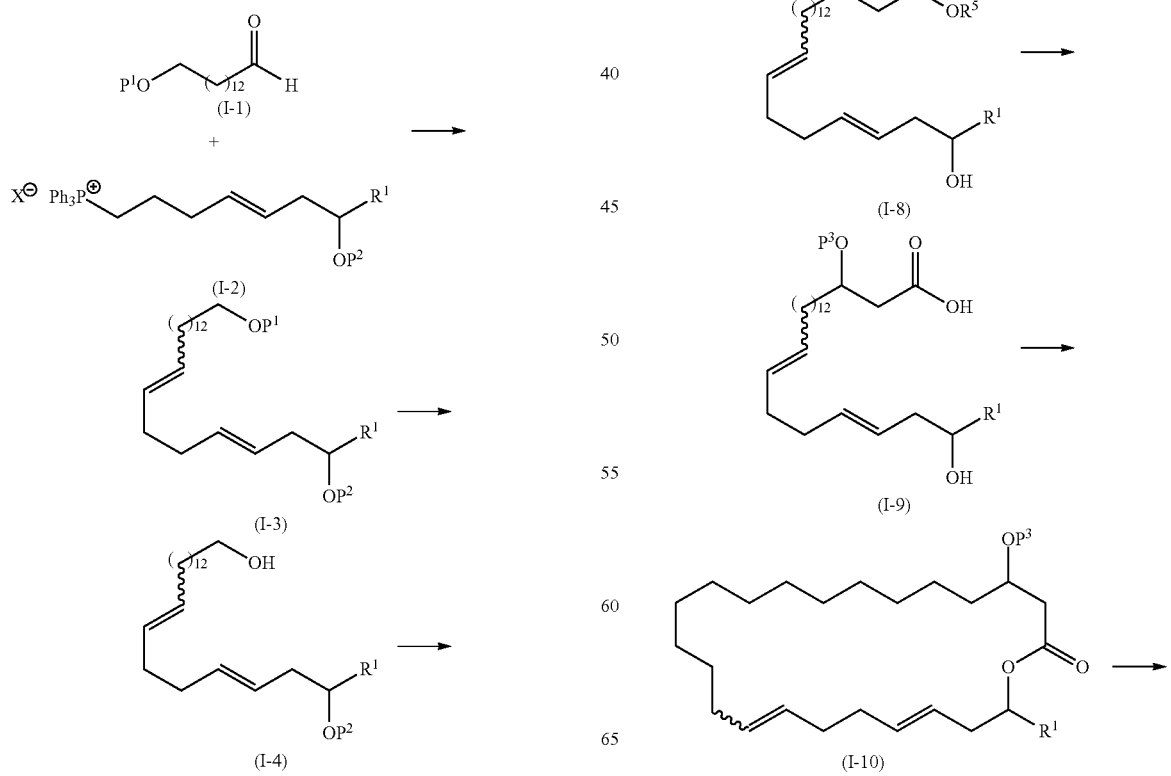

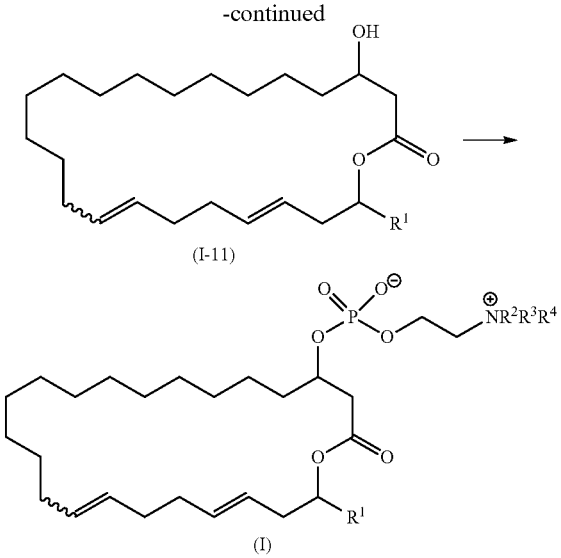

Step 1

According to the present invention, first, a compound represented by the above formula (I-1) and a compound represented by the formula (I-2) are subjected to the Wittig reaction in the presence of a base for coupling to synthesize a compound represented by the formula (I-3). For the base, preferably used are alkyllithium such as butyllithium, aryllithium such as phenyllithium, lithium diisopropylamide, an alkali metal salt of hexamethyldisilazane such as sodium hexamethyldisilazide, and an alkali metal salt of alcohol such as potassium tert-butoxide. There is no particular limitation for the reaction solvent as long as it is stable in the presence of the above base. Preferably used is an ether-based solvent such as tetrahydrofuran and diethyl ether. The above solvents may be used alone, or may be in combination of two or more as a mixed solvent. There is no particular limitation for the reaction temperature, but it is preferably −78° C. to room temperature. In the step 1, the geometrical isomerism of a double bond to be created can be controlled. When a Z-olefin is desired, an alkyl metal salt of hexamethyldisilazane such as sodium hexamethyldisilazide is preferably used as a base. When an E-olefin is desired, alkyllithium such as butyllithium, aryllithium such as phenyllithium may be preferably used in an amount of 2 equivalents or more relative to the compound represented by the formula (I-2).

Step 2

In the step 2, the protecting group P1 in the compound represented by the formula (I-3) is deprotected to synthesize the compound represented by the formula (I-4). There is no particular limitation for the deprotecting agent as long as it is capable of deprotecting the protecting group P1 without damaging the protecting group P2 depending on the chemical properties of the protecting groups P1 and P2.

Step 3

In the step 3, the primary hydroxy group in the compound represented by the formula (I-4) is oxidized to synthesize the compound represented by the formula (I-5). There is no particular limitation for the oxidizing agent as long as it can oxidize a primary hydroxy group to an aldehyde, but for example, sulfur trioxide-pyridine complex, tetrapropylammonium perruthenate, 2,2,6,6-tetramethyl-1-piperidinyloxy radical, pyridinium chlorochromate, pyridinium dichromate, and 1,1,1-triacetoxy-1,1-dihydro-1,2-benziodoxol-3(1H)-one are preferably used.

Step 4

In the step 4, the compound represented by the formula (I-5) is subjected to the aldol reaction to synthesize the compound represented by the formula (I-6). In this step, the aldol reaction is performed using the compound represented by the formula (I-5) as an electrophilic agent and using an enolate capable of extending a carbon chain by two carbon atoms as a nucleophilic agent. For an enolate serving as a nucleophilic agent, preferred is silyl enol ether derived from acetate ester.

Step 5

In the step 5, the compound represented by the formula (I-6) is transesterified to synthesize the compound represented by the formula (I-7). This step is performed by allowing the compound represented by the formula (I-6) to react with an alcohol corresponding to the portion of the alkoxy group of the target molecule.

Step 6

In the step 6, the compound represented by the formula (I-7) is protected, deprotected to synthesize the compound represented by the formula (I-8). There is no particular limitation for the protecting groups P2 and P3 as long as they differ in chemical properties such as stability against other organic compounds.

Step 7

In the step 7, the compound represented by the formula (I-8) is hydrolyzed to synthesize the compound represented by the formula (I-9). There is no particular limitation for the reagent used for hydrolysis as long as it can be used for hydrolysis of an ester, and either alkali or acidic reagents can be preferably used.

Step 8

In the step 8, the compound represented by the formula (I-9) is cyclized to synthesize the compound represented by the formula (I-10). There is no particular limitation for the reagent used for cyclization as long as it can be used for macrolactonization, but for example, 2-methyl-6-nitrobenzoic anhydride (MNBA) is preferably used.

Step 9

In the step 9, the compound represented by the formula (I-10) is deprotected to synthesize the compound represented by the formula (I-11). There is no particular limitation for the deprotecting agent as long as it is appropriately selected according to the chemical properties of the protecting group P3 and can be used without damaging the structure of the compound.

Step 10

In the step 10, the compound represented by the formula (I) is synthesized from the compound represented by the formula (I-11). The reaction is performed by allowing the compound represented by the formula (I-11) to react with a phosphorus compound such as a compound represented by the following formula:

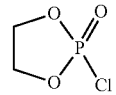

and then with an amine R2R3R4N.

In the present invention, the eushearilides represented by the formula (I) may also be manufactured from the compound represented by the formula (I-7) according to the following scheme.

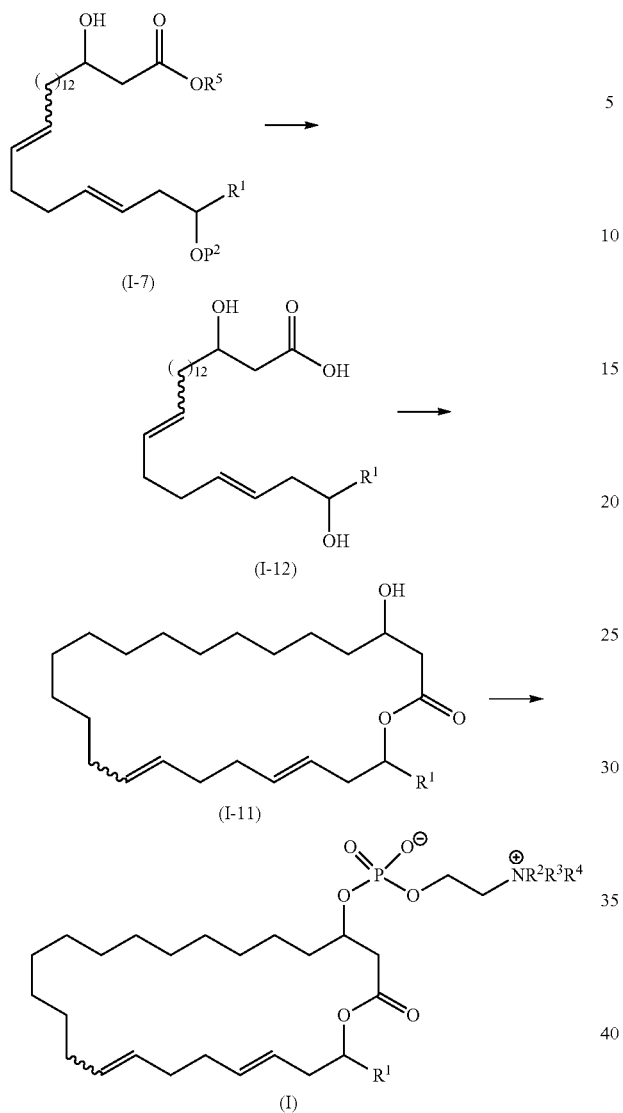

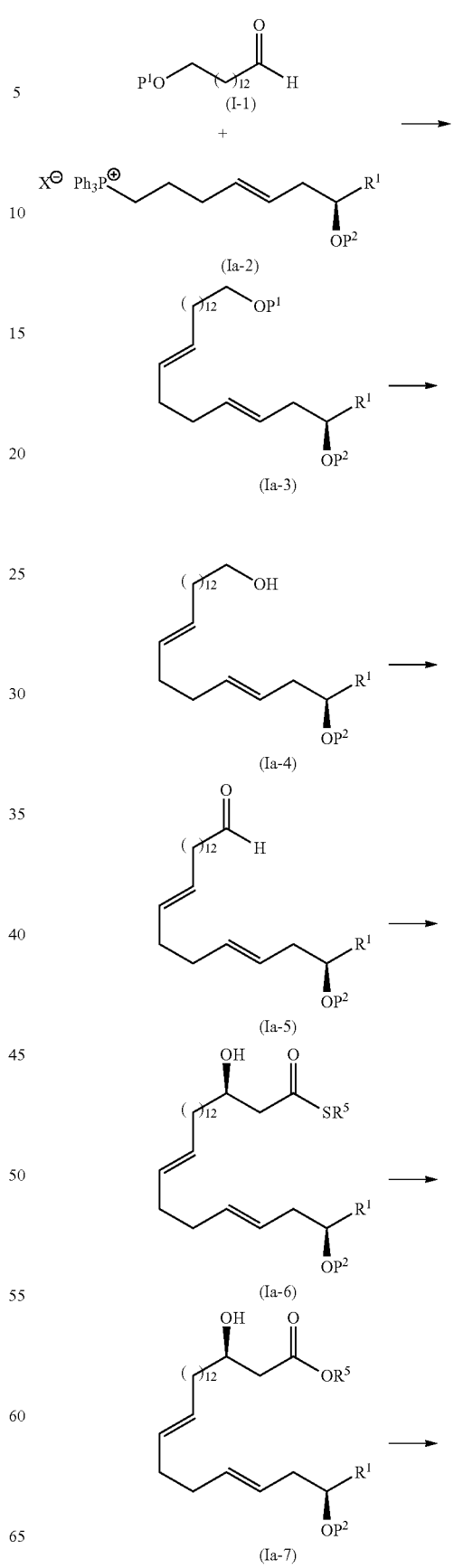

In the method according to the above scheme, the protecting group P2 in the compound represented by the formula (I-7) is deprotected, and the ester portion COOR5 is hydrolyzed to carboxylic acid COOH to synthesize the compound represented by the formula (I-12). There is no particular limitation for the reagents used for deprotection and hydrolysis as long as they do not damage the structure of the compound. The above deprotection and hydrolysis may be performed on a one by one basis, or may be performed simultaneously. Deprotection and hydrolysis may be performed in any order when they are performed on a one by one basis.

Next, the compound represented by the formula (I-12) is cyclized to synthesize the compound represented by the formula (I-11). There is no particular limitation for the reagent used for cyclization as long as it can be used for macrolactonization, but for example, 2-methyl-6-nitrobenzoic anhydride (MNBA) is preferably used.

Finally, the eushearilides represented by the formula (I) are synthesized by a similar way as in the step 10 above.

The above manufacturing method, which is particularly useful for manufacturing eushearilides with controlled stereochemistry, will be described in detail with reference to the following scheme.

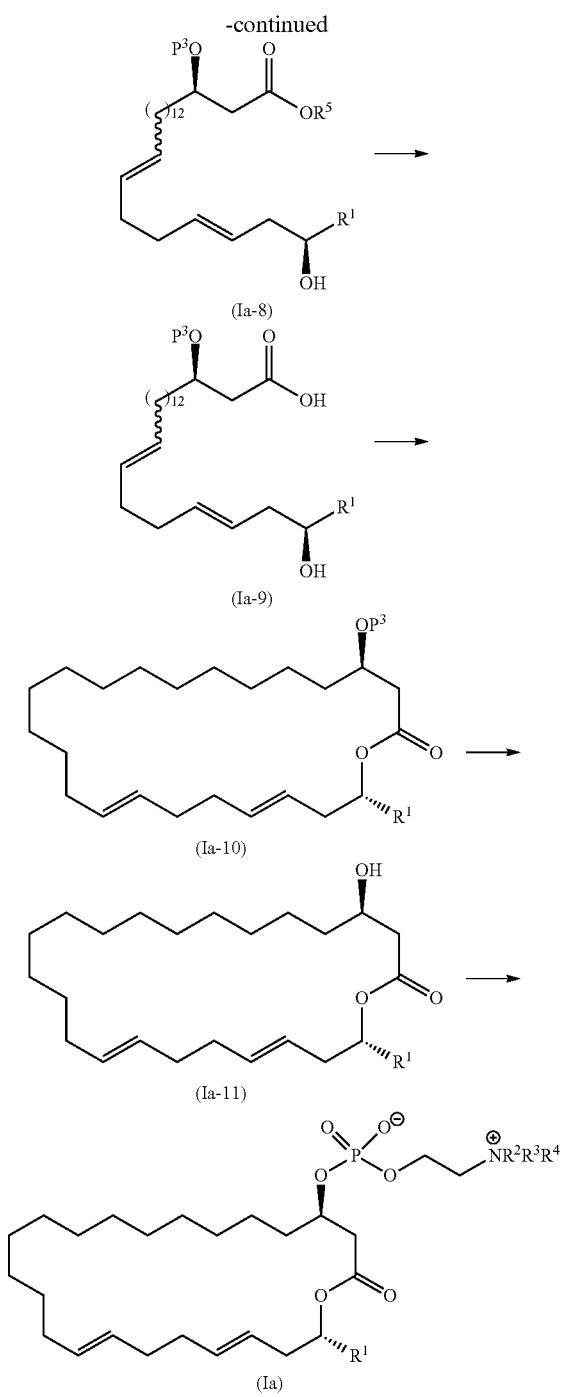

Step 1

The compound represented by the formula (I-1) and the compound represented by the formula (Ia-2) are subjected to the Wittig reaction in the presence of a base for coupling to synthesize the compound represented by the formula (Ia-3). In view of the subsequent steps, an organosilicon-based protecting group such as tert-butyldimethylsilyl group; and a benzyloxymethyl group (BOM) are preferred as the protecting group P1 in the compound represented by the formula (I-1) and the protecting group P2 in the compound represented by the formula (Ia-2), respectively. As reaction conditions for obtaining an E-olefin, preferred are the Schlosser's conditions in which alkyllithium such as butyl-lithium, aryllithium such as phenyllithium may be used in an amount of 2 equivalents or more relative to the compound represented by the formula (Ia-2).

Step 2

In the step 2, the protecting group P1 in the compound represented by the formula (Ia-3) is deprotected to synthesize the compound represented by the formula (Ia-4). There is no particular limitation for the deprotecting agent as long as it is capable of deprotecting the protecting group P1 without damaging the protecting group P2 depending on the chemical properties of the protecting groups P1 and P2. For example, when the protecting group P1 is a tert-butyldimethylsilyl group and the protecting group P2 is a benzyloxymethyl group (BOM), tetrabutylammonium fluoride (TBAF) or a fluorine-based reagent such as hydrofluoric acid is preferably used as the deprotection agent.

Step 3

In the step 3, the primary hydroxy group in the compound represented by the formula (Ia-4) is oxidized to synthesize the compound represented by the formula (Ia-5). There is no particular limitation for the oxidizing agent as long as it can oxidize a primary hydroxy group to an aldehyde, but for example, sulfur trioxide-pyridine complex is preferably used.

Step 4

In the step 4, the compound represented by the formula (Ia-5) is subjected to the aldol reaction to synthesize the compound represented by the formula (Ia-6). This step is performed according to the so-called Mukaiyama aldol reaction in which the compound represented by the formula (Ia-5) is allowed to react with silyl enol ether represented by the following formula:

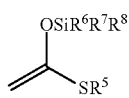

wherein R5 represents a hydrogen atom or an optionally substituted hydrocarbon group, and R6 to R8 independently represent an optionally substituted hydrocarbon group, in the presence of a tin compound and a chiral diamine compound.

As the tin compound, tin triflate is preferably used. As the chiral diamine, for example, compounds represented by the following formula:

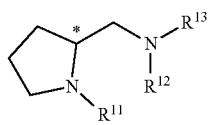

wherein R11 represents a hydrocarbon group, and R12 and R13 independently represent a hydrogen atom or an aryl group, and R12 and R13 may be joined together to form a ring, are preferably used. Among these, a compound represented by the following formula:

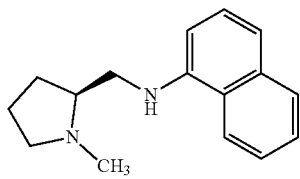

is in particular preferably used. It is noted that a compound may be used in which a tin compound and chiral diamine are pre-complexed.

With regard to the reaction temperature, a low temperature is preferred in view of achieving high stereoselectivity. Specifically, the temperature is preferably −78° C. to room temperature. With regard to the reaction solvent, an aprotic noncoordinating solvent is preferably used. Specifically, a halogen-based solvent such as dichloromethane, a nitrile-based solvent such as propionitrile may be preferably used. Further, a tin(IV) salt such as tributyltin fluoride and dibutyltin diacetate may be further added in order to improve stereoselectivity and yield.

It is noted that the reaction may be performed under conditions appropriately modified from the above reaction conditions as long as the stereoselectivity and yield are not impaired. For example, reaction conditions described in Isamu Shiina, "The Chemical Record," Jan. 25, 2014, vol. 14, pp. 144-183, and other references cited therein may be used.

Step 5

In the step 5, the compound represented by the formula (Ia-6) is transesterified to synthesize the compound represented by the formula (Ia-7). This step is performed by allowing the compound represented by the formula (Ia-6) to react with an alcohol corresponding to the portion of the alkoxy group of the target molecule. Reaction conditions are preferred where silver trifluoroacetate and a base may be added in addition to the aforementioned alcohol.

Step 6

In the step 6, the compound represented by the formula (Ia-7) is protected, deprotected to synthesize the compound represented by the formula (Ia-8). There is no particular limitation for the protecting groups P2 and P3 as long as they differ in chemical properties such as stability against other organic compounds. For example, it is preferred that P2 is benzyloxymethyl (BOM), and P3 is a 4-methoxybenzyl group (PMB).

Step 7

In the step 7, the compound represented by the formula (Ia-8) is hydrolyzed to synthesize the compound represented by the formula (Ia-9). There is no particular limitation for the reagent used for hydrolysis as long as it can be used for hydrolysis of an ester, and either alkali or acidic reagents can be preferably used, but for example, lithium hydroxide is preferably used.

Step 8

In the step 8, the compound represented by the formula (Ia-9) is cyclized to synthesize the compound represented by the formula (Ia-10). There is no particular limitation for the reagent used for cyclization as long as it can be used for macrolactonization. In view of reactivity and efficiency such as yield, 2-methyl-6-nitrobenzoic anhydride (MNBA) is preferably used as a reagent for cyclization.

Step 9

In the step 9, the compound represented by the formula (Ia-10) is deprotected to synthesize the compound represented by the formula (Ia-11). There is no particular limitation for the deprotecting agent as long as it is appropriately selected according to the chemical properties of the protecting group P3, and can be used without damaging the structure of the compound. For example, when P3 is 4-methoxybenzyl (PMB), 2,3-dichloro-5,6-dicyano-p-benzoquinone (DDQ) is preferably used as a deprotection agent.

Step 10

In the step 10, the compound represented by the formula (I) is synthesized from the compound represented by the formula (Ia-11). The reaction is performed by allowing the compound represented by the formula (I-11) to react with a phosphorus compound such as a compound represented by the following formula:

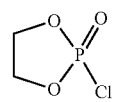

and then with an amine R2R3R4N.

In the present invention, the eushearilides represented by the formula (Ia) may also be manufactured from the compound represented by the formula (Ia-7) according to the following scheme.

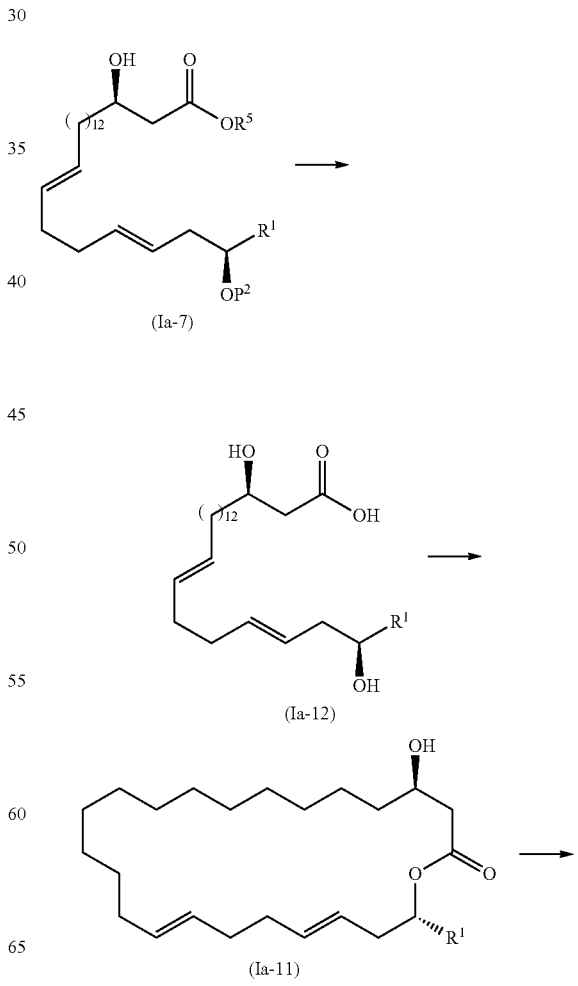

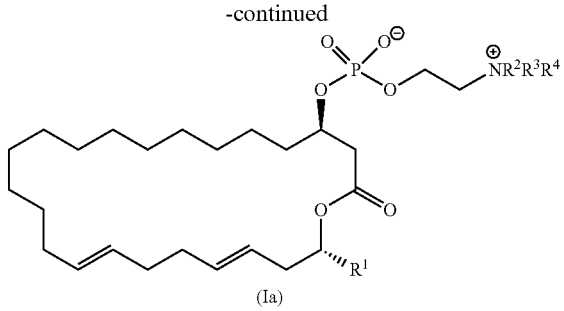

(Ia)

In the method according to the above scheme, the protecting group P2 in the compound represented by the formula (Ia-7) is deprotected, and the ester portion COOR5 is hydrolyzed into carboxylic acid COOH to synthesize the compound represented by the formula (Ia-12). There is no particular limitation for the reagents used for deprotection and hydrolysis as long as they do not damage the structure of the compound. The above deprotection and hydrolysis may be performed on a one by one basis, or may be performed simultaneously. Deprotection and hydrolysis may be performed in any order when they are performed on a one by one basis.

Next, the compound represented by the formula (Ia-12) is cyclized to synthesize the compound represented by the formula (Ia-11). There is no particular limitation for the reagent used for cyclization as long as it can be used for macrolactonization, but for example, 2-methyl-6-nitrobenzoic anhydride (MNBA) is preferably used.

Finally, the eushearilides represented by the formula (Ia) are synthesized in a similar way as in the step 10 described above.

The compound represented by the formula (I-1) can be manufactured according to the following manufacturing scheme.

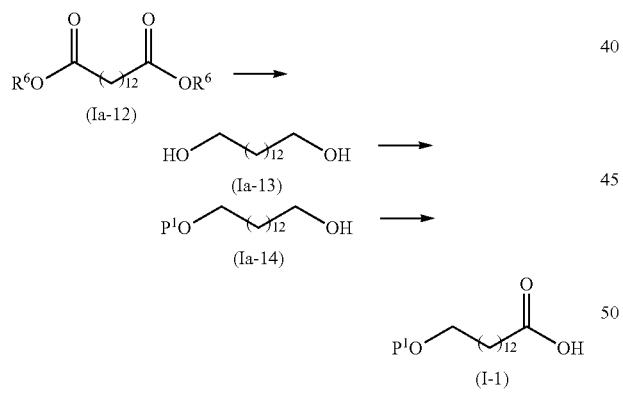

The compound represented by the formula (Ia-12) is reduced with a reducing agent such as lithium aluminum hydride (LAH) to synthesize the compound represented by the formula (Ia-13). A primary hydroxy group at one position in the compound represented by the formula (Ia-13) is protected with the protecting group P1 to synthesize the compound represented by the formula (Ia-14). The primary hydroxy group in the compound represented by the formula (Ia-14) can be oxidized to synthesize the compound represented by the formula (I-1).

The compound represented by the formula (Ia-2) can be manufactured according to the following manufacturing scheme.

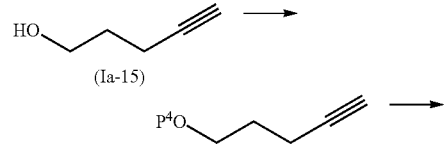

(Ia-15)

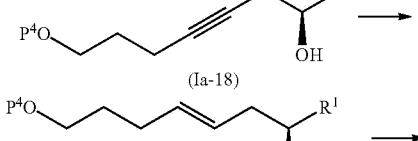

(Ia-16)

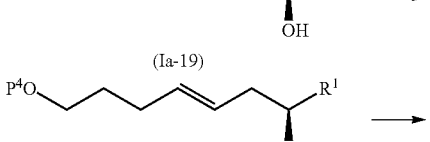

(Ia-18)

(Ia-19)

(Ia-20)

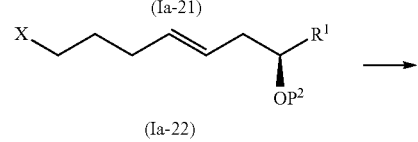

(Ia-21)

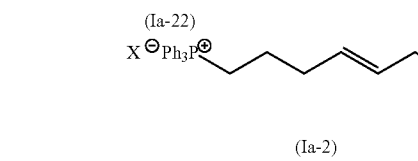

(Ia-22)

(Ia-2)

The hydroxy group in the compound represented by the formula (Ia-15) is protected with P4 to synthesize the compound represented by the formula (Ia-16). There is no particular limitation for the protecting group P4 as long as it can be used as a protecting group for a hydroxy group, but, for example, a tetrahydropyran-2-yl group (THP) is preferred. The compound represented by the formula (Ia-16) is allowed to react with a base such as butyllithium to obtain acetylide, and then allowed to react with an epoxy compound represented by the formula (Ia-17):

(Ia-17)

wherein R1 represents a hydrogen atom or an optionally substituted hydrocarbon group, to synthesize the compound represented by the formula (Ia-18). When R1 in the formula (Ia-17) is an optionally substituted hydrocarbon group, an asymmetrical carbon is introduced in this reaction. Therefore, a compound having an absolute configuration different from that of the compound represented by the formula (Ia-18) can be obtained when an optically active epoxy compound is used having an absolute configuration different from the above chemical structural formula. Thus, the stereochemistry at Position 23 of the 24-member macrolide can controlled via the absolute configuration of an optically active epoxy compound to be used.

The triple bond in the compound represented by the formula (Ia-18) is reduced with a reducing agent such as lithium aluminum hydride to synthesize the compound represented by the formula (Ia-19). The secondary hydroxy group in the compound represented by the formula (Ia-19) is protected with the protecting group P2 to synthesize the compound represented by the formula (Ia-20). The protecting group P4 in the compound represented by the formula (Ia-20) is deprotected to synthesize the compound represented by the formula (Ia-21). The hydroxy group in the compound represented by the formula (Ia-21) is halogenated to synthesize the compound represented by the formula (Ia-22). The compound represented by the formula (Ia-22) can be allowed to react with triphenylphosphine to synthesize the compound represented by the formula (Ia-2).

In drug discovery research, manufacturing various derivatives from one intermediate is important in terms of time and cost. In view of this, according to the present invention, the compound represented by the following formula (II):

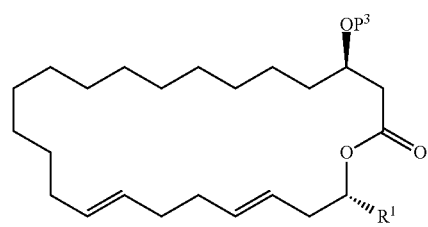

(II)

wherein R1 represents a hydrogen atom or an optionally substituted hydrocarbon group, and P3 represents a hydrogen atom or a protecting group, is an important intermediate, from which various derivatives can be manufactured, for example, by taking advantage of the functionality of the secondary alcohol portion.

According to the above manufacturing scheme, various eushearilides, for example, the compounds represented by the formulas (A) to (H) shown below can be manufactured. It should be noted that the optically active eushearilides represented by the formulas (A) and (E) to (G) are novel compounds not found in the literature.

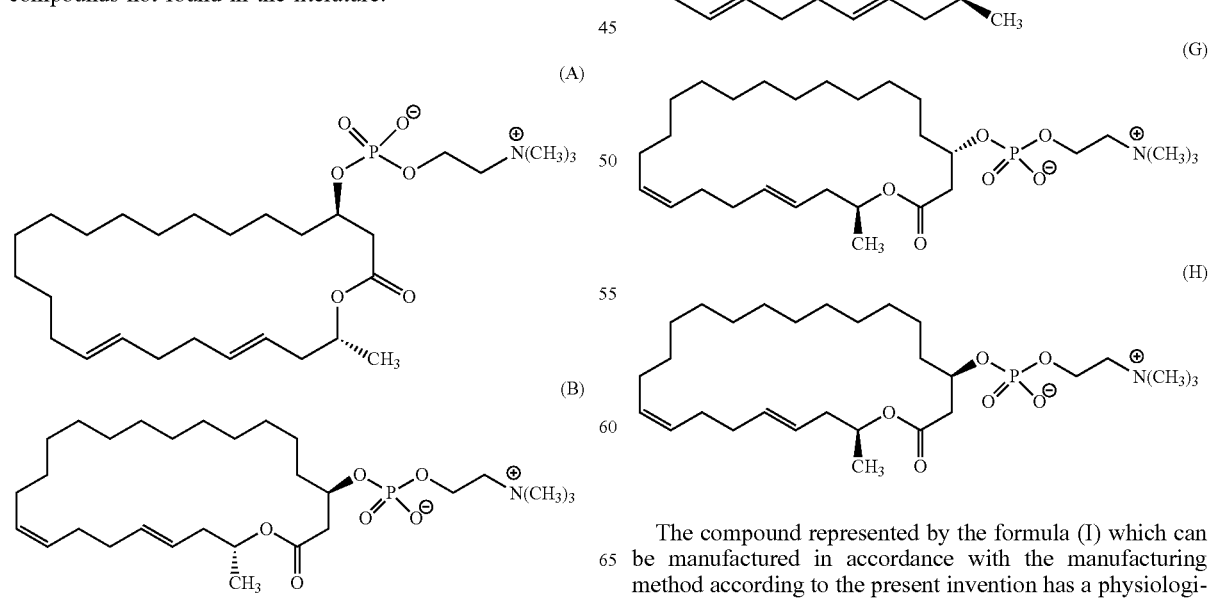

(A)

(B)

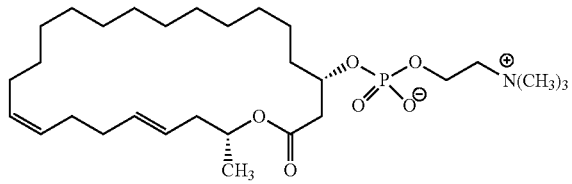

(C)

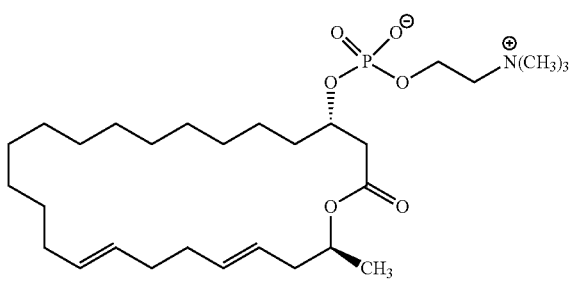

(D)

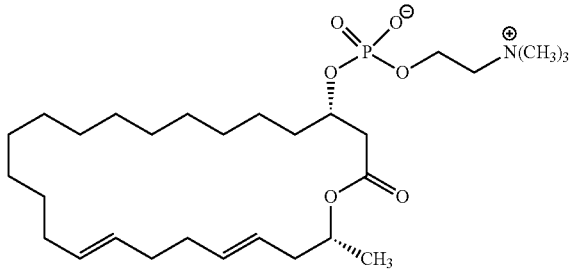

(E)

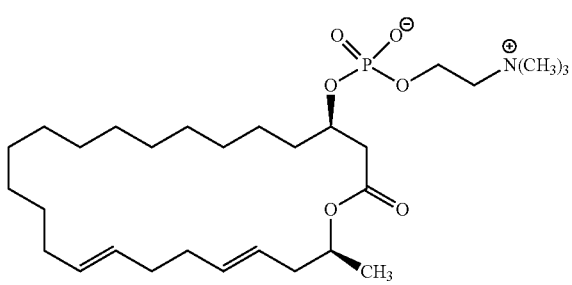

(F)

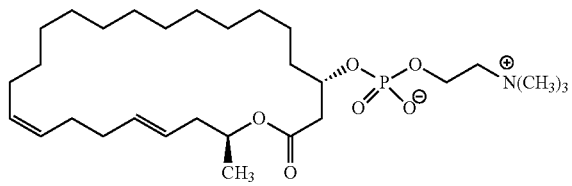

(G)

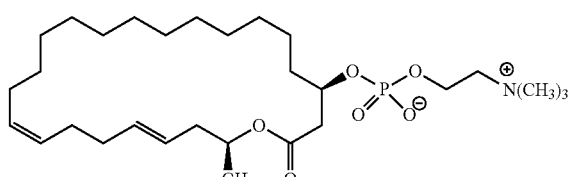

(H)

The compound represented by the formula (I) which can be manufactured in accordance with the manufacturing method according to the present invention has a physiological activity, and thus can be used as a medicament.

When the compound represented by the formula (I) according to the present invention is used as a medicament, formulation adjuvants such as an excipient, a carrier, and a diluent which can be commonly used for formulation may be mixed in an appropriate way. These may be conventionally administrated orally or parenterally in the forms of tablet, capsule, powder, syrup, granule, pill, suspension, emulsion, solution, powdered formulation, suppository, eye drop, nasal drop, ear drop, adhesive patch, ointment, or injectable formulation, or the like. Further, the mode of administration, a dose, and the frequency of administration can be appropriately selected depending on the age, weight, and conditions of a patient. Usually, a dose of 0.01 to 1000 mg/kg per day may be administrated orally or parenterally (for example, injection, infusion, rectum administration, and the like) to an adult patient. The dose may be administrated in one to several portions. The compound represented by the formula (I) of the present invention is useful for treating local or systemic infection in human and animal which may be caused by gram positive, gram negative, anaerobic, acid-fast bacteria and the like.

The compound represented by the formula (I) of the present invention is useful for treating or preventing resistant bacterial infection. Resistant bacteria include methicillin-resistant *Staphylococcus aureus* (MRSA), vancomycin-resistant *Enterococcus* (VRE), vancomycin-resistant *Staphylococcus aureus* (VRSA), and the like.

The term "therapeutically effective amount" as used in the present invention refers to the amount of a compound which can provide a desired biological outcome such as preventing the onset of bacterial infection, mitigating conditions of bacterial infection, stopping aggravation of bacterial infection, or ameliorating clinical symptoms of bacterial infection. The term "subject" as used in the present invention refers to mammal, plant, lower animal, or cell culture medium. In one embodiment, the subject is a human patient or another animal patient in need of antibacterial treatment. The term "administration" as used in the present invention means that the compound according to the present invention (for example, the compound represented by the formula (I)) is introduced into a subject in need of treatment. The object is preferably mammal, more preferably human.

EXAMPLES

Below, Examples of the present invention will be described along with specific synthesis schemes, but the present invention shall not be particularly limited.

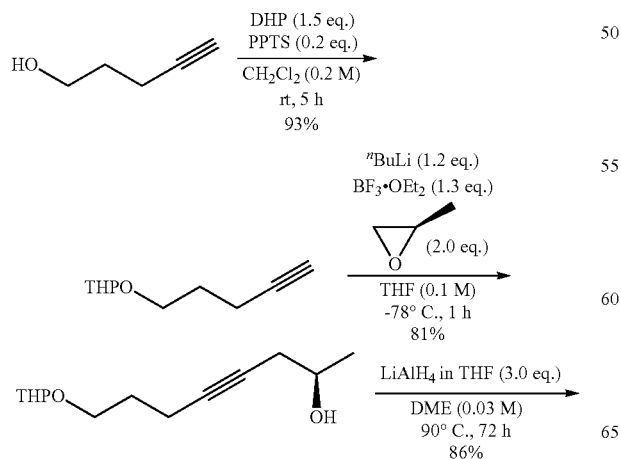
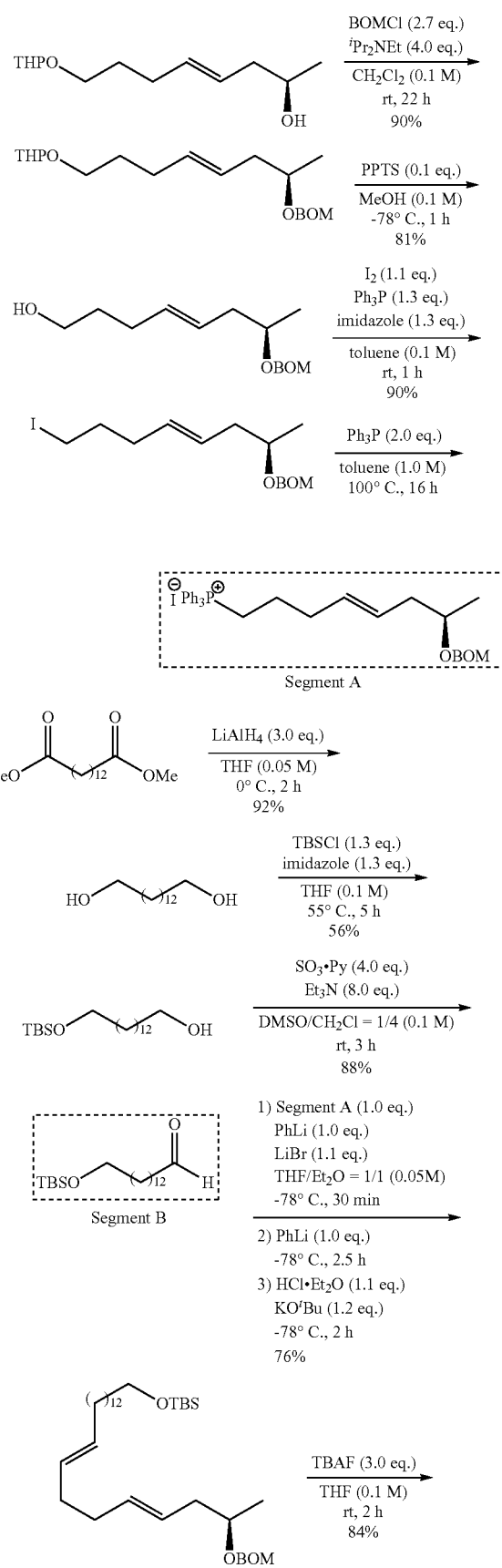

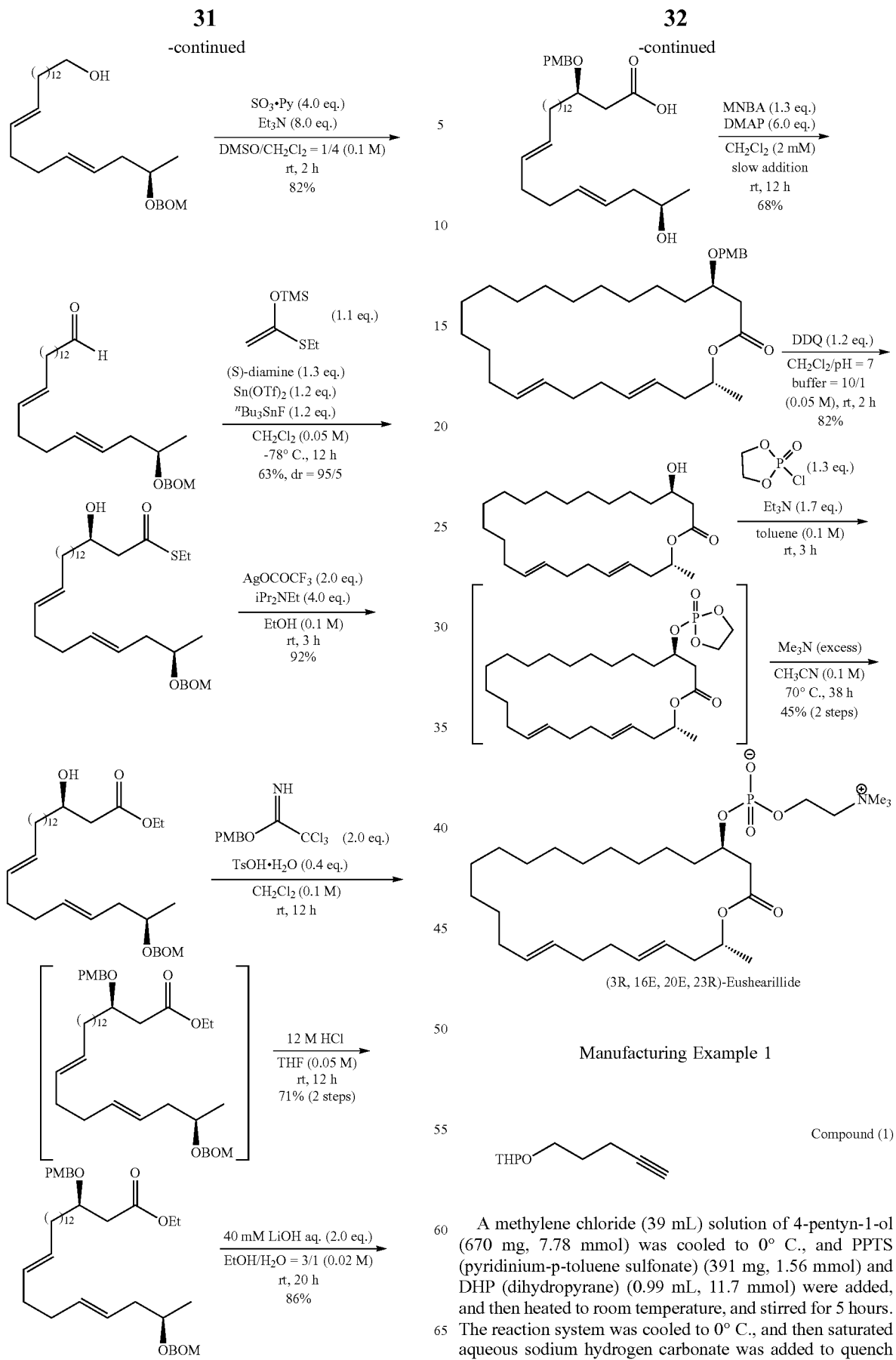

Manufacturing Example 1

Compound (1)

A methylene chloride (39 mL) solution of 4-pentyn-1-ol (670 mg, 7.78 mmol) was cooled to 0° C., and PPTS (pyridinium-p-toluene sulfonate) (391 mg, 1.56 mmol) and DHP (dihydropyrane) (0.99 mL, 11.7 mmol) were added, and then heated to room temperature, and stirred for 5 hours. The reaction system was cooled to 0° C., and then saturated aqueous sodium hydrogen carbonate was added to quench the reaction. The organic phase was fractionated, and the aqueous phase was then extracted 3 times with methylene chloride. Fractions of the organic phase were combined together, and washed with water and saturated brine, and dried over anhydrous sodium sulfate. The solution was filtered, and then concentrated under reduced pressure. The resulting crude product was purified by silica gel column chromatography (Hexane/ethyl acetate=12/1) to obtain a compound (1) (1.22 g, 93%).

Rf=0.4 (hexane/ethyl acetate=10/1)

1H-NMR (500 MHz, CDCl3): δ4.60, 3.89-3.81, 3.53-3.46, 2.31, 1.94, 1.82, 1.71, 1.59-1.50 13C-NMR (125 MHz, CDCl3): δ94.4, 82.6, 70.1, 68.0, 65.2, 39.9, 38.3, 35.7, 31.0, 27.7

HR-MS (ESI-TOF): m/z calcd for C10H16O2Na [M+Na]+: 191.1043, found: 191.1040.

IR (neat): 3302, 2947, 2869 cm-1

Manufacturing Example 2

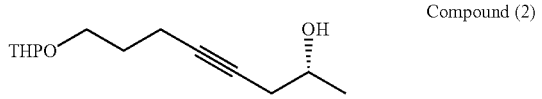

Compound (2)

A THF (tetrahydrofuran) (36 mL) solution of the compound (1) (613 mg, 3.64 mmol) was cooled to −78° C., and nBuLi (2.6 M in hexane, 1.68 mL, 4.37 mmol) was added dropwise, and then stirred for 20 minutes. After BF3.OEt2 (boron trifluoride-diethyl ether complex) (0.59 mL, 4.73 mmol) was slowly added dropwise, and then stirred for 10 minutes, and (R)-propylene oxide (0.51 mL, 7.28 mmol) was added dropwise, and stirred for 1 hour while the temperature was maintained at −78° C. Saturated aqueous ammonium chloride was added to quench the reaction. The organic phase was fractionated, and the aqueous phase was then extracted 3 times with ethyl acetate. Fractions of the organic phase were combined together, and washed with saturated brine, and dried over anhydrous sodium sulfate. The solution was filtered, and then concentrated under reduced pressure. The resulting crude product was purified by silica gel column chromatography (hexane/ethyl acetate=3/1) to obtain a compound (2) (663 mg, 81%).

Rf=0.4 (hexane/ethyl acetate=3/1)

1H-NMR (500 MHz, CDCl3): δ4.59, 3.91-3.82, 3.53-3.45, 2.38-2.27, 2.07, 1.83-1.68, 1.61-1.50, 1.23

13C-NMR (125 MHz, CDCl3): δ98.8, 82.4, 76.6, 66.5, 65.9, 62.3, 30.7, 29.4, 29.0, 25.4, 22.2, 19.5, 15.6

HR-MS (ESI-TOF): m/z calcd for C13H22O3Na [M+Na]+: 249.1461, found: 249.1458.

IR (neat): 3471, 2947 cm-1

Manufacturing Example 3

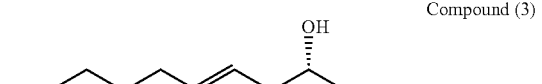

Compound (3)

A 1,2-dimethoxyethane (21 mL) solution of the compound (2) (145 mg, 0.641 mmol) was cooled to 0° C., and LiAlH4 (1.0 M in THF, 1.9 mL, 1.9 mmol) was added, and then was heated to reflux at 90° C. for 72 hours. The reaction system was cooled to 0° C., and methanol and saturated aqueous potassium sodium tartrate were added to quench the reaction. The organic phase was fractionated, and then the aqueous phase was extracted 3 times with diethyl ether. Fractions of the organic phase were combined together, and washed with water and saturated brine, and dried over anhydrous sodium sulfate. The solution was filtered, and then concentrated under reduced pressure. The resulting crude product was purified by silica gel thin layer chromatography (hexane/ethyl acetate=3/1) to obtain a compound (3) (126 mg, 86%).

Rf=0.5 (hexane/ethyl acetate=1/1)

1H-NMR (500 MHz, CDCl3): δ5.55, 5.44, 4.56, 3.90-3.72, 3.49, 3.39, 2.23-2.04, 1.83, 1.73-1.65, 1.60-1.50, 1.18

13C-NMR (125 MHz, CDCl3): δ133.8, 126.4 (126.4), 98.9, 67.2, 67.1, 66.9, 62.4, 42.6 (42.5), 30.8, 29.4 (29.3), 25.5, 22.6, 19.7

HR-MS (ESI-TOF): m/z calcd for C13H24O3Na [M+Na]+: 251.1618, found: 251.1611.

IR (neat): 3433, 2939, 2877 cm-1

Manufacturing Example 4

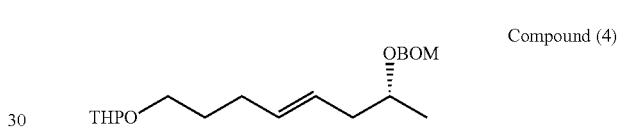

Compound (4)

A methylene chloride (7.5 mL) solution of the compound (3) (171 mg, 0.748 mmol) was cooled to 0° C., and diisopropylethylamine (0.52 mL, 2.98 mmol), BOMCl (butoxymethylchloride) (0.31 mL, 2.36 mmol), and TBAI (tetrabutylammonium iodide) (55 mg, 0.15 mmol) were added, and then stirred for 22 hours. Saturated aqueous sodium hydrogen carbonate was added to quench the reaction. The organic phase was fractionated, and then the aqueous phase was extracted 3 times with methylene chloride. Fractions of the organic phase were combined together, and washed with water and saturated brine, and dried over anhydrous sodium sulfate. The solution was filtered, and then concentrated under reduced pressure. The resulting crude product was purified by silica gel thin layer chromatography (hexane/ethyl acetate=5/1) to obtain a compound (4) (235 mg, 90%).

Rf=0.7 (hexane/ethyl acetate=2/1)

1H-NMR (500 MHz, CDCl3): δ7.35-7.27, 5.48, 4.79, 4.62, 4.57, 3.88-3.71, 3.49, 3.38, 2.28, 2.16, 2.09, 1.81, 1.69, 1.54, 1.17

13C-NMR (125 MHz, CDCl3): δ138.0, 132.5, 127.8, 127.6, 126.5, 98.8, 92.8, 73.0, 62.3, 40.0, 30.7, 29.5, 29.3, 25.5, 19.9, 19.6

HR-MS (ESI-TOF): m/z calcd for C21H32O4Na [M+Na]+: 371.2193, found: 371.2186.

IR (neat): 2988, 2885 cm-1

Manufacturing Example 5

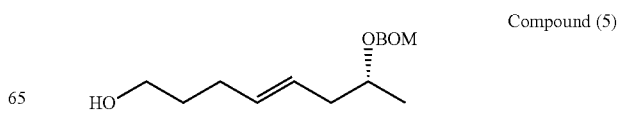

Compound (5)

PPTS (7.7 mg, 0.03087 mmol) was added to a methanol (3.1 mL) solution of the compound (4) (107 mg, 0.308 mmol), and then heated to 55° C. and stirred for 5 hours. The reaction system was returned to room temperature, and saturated aqueous sodium hydrogen carbonate was added to quench the reaction. The organic phase was fractionated, and then the aqueous phase was extracted 3 times with chloroform. Fractions of the organic phase were combined together, and washed with water and saturated brine, and dried over anhydrous sodium sulfate. The solution was filtered, and then concentrated under reduced pressure. The resulting crude product was purified by silica gel thin layer chromatography (hexane/ethyl acetate=3/1) to obtain a compound (5) (81.3 mg, 84%).

Rf=0.3 (hexane/ethyl acetate=3/1)

1H-NMR (500 MHz, CDCl3): δ7.35-7.26 (m, 5H, BOM), 5.52 (dt, J=15.2, 6.8 Hz, 1H, 4-H or 5-H), 5.47 (dt, J=15.2, 6.8 Hz, 1H, 4-H or 5-H), 4.79 (m, 2H, BOM), 4.62 (m, 2H, BOM), 3.81 (ddq, J=6.0, 6.0, 6.0 Hz, 1H, 7-H), 3.64 (t, J=6.4 Hz, 2H, 1-H), 2.28 (ddd, J=13.2, 6.0, 6.8 Hz, 1H, 6-H), 2.18 (ddd, J=13.2, 6.8, 6.0 Hz, 1H, 6-H), 2.10 (dt, J=6.8, 6.0 Hz, 2H, 3-H), 1.63 (tt, J=6.4, 6.0 Hz, 2H, 2-H), 1.18 (d, J=6.0 Hz, 3H, 8-H)

13C-NMR (125 MHz, CDCl3): δ138.1 (BOM), 132.4 (C4), 128.4 (BOM), 127.8 (BOM), 127.6 (C5), 126.8 (BOM), 92.8 (BOM), 72.9 (BOM), 69.3 (C7), 40.0 (C6), 32.3 (C2), 29.1 (C3), 19.9 (C8)

IR (neat): 3409, 2931 cm-1

[α]D20 +7.73 (c1.17, CHCl3)

Manufacturing Example 6

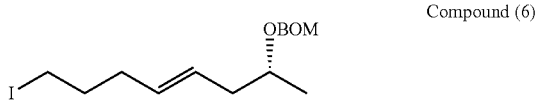

Compound (6)

Imidazole (440 mg, 6.45 mmol), PPh3 (triphenylphosphine) (1.69 g, 6.45 mmol), and iodine (1.39 g, 5.46 mmol) were sequentially added to a toluene (50 mL) solution of the compound (5) (1.31 g, 4.96 mmol), and stirred at room temperature for 1 hour. The reaction system was cooled to 0° C., and then saturated aqueous sodium thiosulfate was added to quench the reaction. The organic phase was fractionated, and the aqueous phase was then extracted 3 times with diethyl ether. Fractions of the organic phase were combined together, and washed with water and saturated brine, and dried over anhydrous sodium sulfate. The solution was filtered, and then concentrated under reduced pressure. The resulting crude product was purified by silica gel column chromatography (hexane/ethyl acetate=10/1) to obtain a compound (6) (1.67 g, 90%).

Rf=0.4 (hexane/ethyl acetate=10/1)

1H-NMR (500 MHz, CDCl3): δ7.35-7.26 (m, 5H, BOM), 5.52 (dt, J=15.2, 6.8 Hz, 1H, 4-H or 5-H), 5.42 (dt, J=15.2, 6.8 Hz, 1H, 4-H or 5-H), 4.79 (m, 2H, BOM), 4, 62 (m, 2H, BOM), 3.80 (ddq, J=6.4, 6.2, 6.0 Hz, 1H, 7-H), 3.17 (t, J=6.8 Hz, 2H, 1-H), 2.28 (ddd, J=14.0, 6.8, 6.4 Hz, 1H, 6-H), 2.18 (ddd, J=14.0, 6.8, 6.2 Hz, 1H, 6-H), 2.11 (dt, J=6.8, 6.8 Hz, 2H, 3-H), 1.87 (tt, J=6.8, 6.8 Hz, 2H, 2-H), 1.18 (d, J=6.4 Hz, 3H, 8-H)

13C-NMR (125 MHz, CDCl3): δ138.0 (BOM), 130.6 (C4), 128.4 (BOM), 127.9 (BOM), 127.8 (C5), 127.6 (BOM), 92.9 (BOM), 72.9 (BOM), 79.3 (C7), 40.0 (C6), 33.2 (C3), 32.9 (C2), 20.0 (C8), 6.4 (C1)

HR-MS (ESI-TOF): m/z calcd for C16H23O2Na [M+Na]+: 397.0635, found: 397.0646.

IR (neat): 3031, 2962, 2931, 2892 cm-1

[α]D20 +5.25 (c1.27, CHCl3)

Manufacturing Example 7

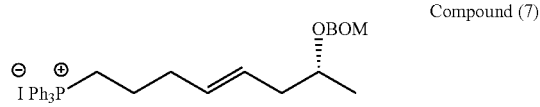

Compound (7)

PPh3 (4.17 g, 15.9 mmol) was added to a toluene (8.0 mL) solution of the compound (6) (2.89 g, 7.96 mmol), and heated to reflux at 100° C. for 16 hours. The solvent was distilled away under reduced pressure, and then the resulting mixture was washed 10 times or more with a small amount of the mixed solvent of methylene chlorides and hexane. The resulting crude product was directly used in the next reaction without performing purification but after determining the purity thereof by 1H-NMR.

1H-NMR (500 MHz, CDCl3): δ7.82 (m, 9H, Ar), 7.77 (m, 6H, Ar), 7.35-7.26 (m, 5H, BOM), 5.51 (dt, J=15.2, 6.8 Hz, 1H, 4-H or 5-H), 5.38 (dt, J=15.2, 6.8 Hz, 1H, 4-H or 5-H), 4.71 (m, 2H, BOM), 4.54 (m, 2H, BOM), 3.75 (ddq, J=6.8, 6.4, 6.4 Hz, 1H, 7-H), 3.66 (dt, J=12.6, 3.3 Hz, 1H, 1-H), 3.62 (dt, J=12.6, 3.3 Hz, 1H, 1-H), 2.39 (dt, J=7.2, 6.8 Hz, 2H, 3-H), 2.24 (ddd, J=14.4, 6.8, 6.8 Hz, 1H, 6-H), 2.14 (ddd, J=14.4, 6.8, 6.4 Hz, 1H, 6-H), 1.71 (dtt, J=15.2, 7.2, 3.3 Hz, 2H, 2-H), 1.13 (d, J=6.4 Hz, 3H, 8-H)

Manufacturing Example 8

Compound (8)

A THF (280 mL) solution of LiAlH4 (1.73 g, 45.6 mmol) was cooled to 0° C., and a THF (20 mL) solution of dimethyl tetradecanedioate (4.35 g, 15.2 mmol) was slowly added dropwise. It was stirred for 2 hours while maintaining the temperature at 0° C., and the reaction was then quenched with methanol and 1N HCl. The organic phase was fractionated, and then the aqueous phase was extracted 3 times with diethyl ether. Fractions of the organic phase were combined together, and washed with water and saturated brine, and dried over anhydrous sodium sulfate. The solution was filtered, and then concentrated under reduced pressure to obtain a compound (8) (3.22 g, 92%).

Rf=0.3 (chloroform/CH3OH=6/1)

1H-NMR (500 MHz, CDCl3): δ3.65, 1.58, 1.33

13C-NMR (125 MHz, CDCl3): δ63.1, 32.8, 29.6, 29.6, 29.5, 29.4, 25.7

IR (film): 3409, 3347, 2923, 2854 cm-1

Manufacturing Example 9

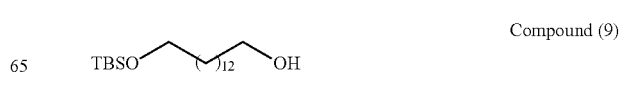

Compound (9)

Imidazole (354 mg, 5.20 mmol) was added to a THF (40 mL) solution of the compound (8) (922 mg, 4.00 mmol), and cooled to 0° C., and TBSCl (tert-butyldimethylchlorosilane) (784 mg, 5.20 mmol) was added. This was heated to 55° C., and stirred for 5 hours, and the reaction was then quenched with saturated aqueous ammonium chloride. The organic phase was fractionated, and then the aqueous phase was extracted 3 times with diethyl ether. Fractions of the organic phase were combined together, and washed with water and saturated brine, and dried over anhydrous sodium sulfate. The solution was filtered, and then concentrated under reduced pressure. The resulting crude product was purified by silica gel column chromatography (hexane/ethyl acetate=10/1) to obtain a compound (9) (743 mg, 56%).

Rf=0.2 (hexane/ethyl acetate=5/1)

1H-NMR (500 MHz, CDCl3): δ3.60, 2.28, 1.65-1.23, 0.89, 0.063

13C-NMR (125 MHz, CDCl3): δ63.4, 63.1, 32.9, 32.8, 29.6, 29.6, 29.6, 29.4, 29.4, 26.0, 25.8, 25.7, 25.6, −5.25

HR-MS (ESI-TOF): m/z calcd for C20H44O2SiNa [M+Na]+: 367.3003, found: 367.3001.

IR (neat): 3394, 2927, 2865 cm-1

Manufacturing Example 10

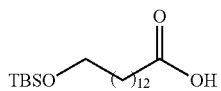

Compound (10)

Et3N (triethylamine) (1.1 mL, 8.0 mmol) was added to a mixed solution of methylene chloride (8.0 mL) and DMSO (dimethyl sulfoxide) (2.0 mL) of the compound (9) (344 mg, 1.0 mmol), and cooled to 0° C., and SO3.Py complex (sulfur trioxide-pyridine complex) (637 mg, 4.0 mmol) was added. It was heated to room temperature, and stirred for 2 hours. The reaction was then quenched with saturated aqueous ammonium chloride. The organic phase was fractionated, and then the aqueous phase was extracted 3 times with ethyl acetate. Fractions of the organic phase were combined together, and washed with water and saturated brine, and dried over anhydrous sodium sulfate. The solution was filtered, and then concentrated under reduced pressure. The resulting crude product was purified by silica gel thin layer chromatography (hexane/ethyl acetate=5/1) to obtain a compound (10) (302 mg, 88%).

Rf=0.4 (hexane/ethyl acetate=10/1)

1H-NMR (500 MHz, CDCl3): δ9.77, 3.60, 2.40, 1.67-1.46, 1.26, 0.89, 0.045

13C-NMR (125 MHz, CDCl3): δ202.9, 63.3, 43.9, 32.9, 29.6, 29.6, 29.6, 29.4, 29.4, 29.3, 29.2, 26.0, 25.8, 22.1, 18.4, −5.26

HR-MS (ESI-TOF): m/z calcd for C20H42O2SiNa [M+Na]+: 365.2846, found: 365.2839.

IR (neat): 2927, 2858, 1724 cm-1

Example 1

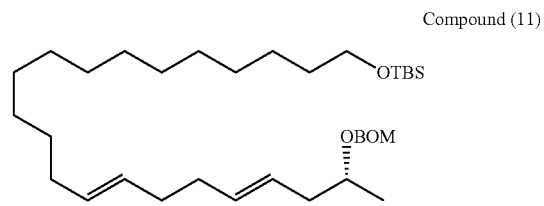

Compound (11)

A THF (1.4 mL) solution of the compound (7) (46 mg, 0.0723 mmol) was cooled to −78° C., and lithium bromide (69 mg, 0.0795 mmol) and PhLi (phenyllithium) (1.6 M in butyl ether, 0.05 mL, 0.0723 mmol) were added, and stirred for 30 minutes. This was slowly added dropwise to a diethyl ether (1.4 mL) solution of the compound (10) (25 mg, 0.0723 mmol) cooled to −78° C. using a cannula. After the dropwise addition was ended, PhLi (1.6 M in butyl ether, 0.05 mL, 0.0723 mmol) was added, and stirred for 2.5 hours while maintaining the temperature at −78° C. HCl.Et2O (hydrogen chloride-diethyl ether) (1.0 M in Et2O, 0.08 mL, 0.0795 mmol) and KOtBu (potassium tert-butoxide) (1.0 M in Et2O, 0.09 mL, 0.0868 mmol) were added sequentially, and stirred at −78° C. for 2 hours. Water was added to quench the reaction. The organic phase was fractionated, and then the aqueous phase was extracted 3 times with diethyl ether. Fractions of the organic phase were combined together, and washed with saturated brine, and dried over anhydrous sodium sulfate. The solution was filtered, and then concentrated under reduced pressure. The resulting crude product was purified by silica gel thin layer chromatography (hexane/ethyl acetate=10/1) to obtain a compound (11) (28 mg, 76%).

Rf=0.53 (hexane/ethyl acetate=10/1)

1H-NMR (500 MHz, CDCl3): δ7.35-7.28 (m, 5H, BOM), 5.50-5.34 (m, 4H, 14-H, 15-H, 18-H, 19-H), 4.79 (q, J=7.2 Hz, 2H, BOM), 4.62 (q, J=9.2 Hz, 2H, BOM), 3.79 (sx, J=6.3 Hz, 1H, 21-H), 3.59 (t, J=6.30 Hz, 2H, 1-H), 2.22 (ddd, J=10.0, 6.9, 6.3 Hz, 1H, 20-H), 2.17 (ddd, J=10.0, 6.9, 6.3 Hz, 1H, 20-H), 2.04 (m, 4H, 13-H, 16-H), 1.95 (m, 2H, 17-H), 1.50 (m, 2H, 2-H), 1.31-1.25 (m, 20H, 3-H to 12-H), 1.17 (d, J=6.30 Hz, 3H, 22-H), 0.893 (s, 9H, TBS), 0.046 (s, 6H, TBS)

13C-NMR (125 MHz, CDCl3): δ138.0 (BOM), 132.7 (C19), 130.8 (C14), 129.5 (C15), 128.4 (BOM), 127.8 (C18), 127.6 (BOM), 126.2 (BOM), 92.8 (BOM), 73.0 (C21), 69.3 (BOM), 63.4 (C1), 40.1 (C20), 32.9 (C16 or C17), 32.8 (C16 or C17), 32.6, 32.6, 29.7, 29.6, 29.6, 29.5, 29.2, 26.0, 25.8 (C2 to C13), 19.9 (C22), 18.4 (TBS), −5.23 (TBS)

HR-MS (ESI-TOF): m/z calcd for C36H64O3SiNa [M+Na]+: 595.4517, found: 595.4494.

IR (neat): 2923, 2854 cm-1

[α]D20 +4.39 (c1.04, CHCl3)

Example 2

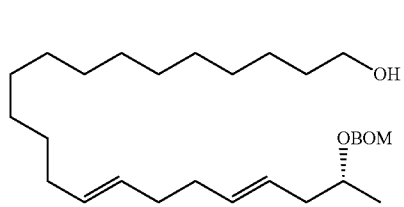

Compound (12)

A THF (15 mL) solution of the compound (11) (860 mg, 1.50 mL) was cooled to 0° C., and TBAF (tetrabutylammonium fluoride) (1.0 M in THF, 4.5 mL, 4.5 mmol) was added, and stirred at room temperature for 2 hours. The reaction system was cooled to 0° C., and then saturated aqueous sodium hydrogen carbonate was added to quench the reaction. The organic phase was fractionated, and then aqueous phase was extracted 3 times with ethyl acetate. Fractions of the organic phase were combined together, and washed with saturated brine, and dried over anhydrous sodium sulfate. The solution was filtered, and then concentrated under reduced pressure. The resulting crude product was purified by silica gel chromatography (hexane/ethyl acetate=10/1) to obtain a compound (12) (577 mg, 84%).

Rf=0.43 (hexane/ethyl acetate=3/1)

1H-NMR (500 MHz, CDCl3): δ7.36-7.27 (m, 5H, BOM), 5.51-5.33 (m, 4H, 14-H, 15-H, 18-H, 19-H), 4.79 (q, J=7.2 Hz, 2H, BOM), 4.61 (m, 2H, BOM), 3.79 (sx, J=6.3 Hz, 1H, 21-H), 3.64, 3.51 (t, J=6.30 Hz, 2H, 1-H), 2.40, 2.28 (ddd, J=10.0, 6.9, 6.3 Hz, 1H, 20-H), 2.16 (ddd, J=10.0, 6.9, 6.3 Hz, 1H, 20-H), 2.04 (m, 4H, 13-H, 16-H), 1.95 (m, 2H, 17-H), 1.56 (m, 2H, 2-H), 1.39, 1.25, 1.17

13C-NMR (125 MHz, CDCl3): δ138.0 (BOM), 132.7 (C19), 130.8 (C14), 129.5 (C15), 128.4 (BOM), 127.9 (C18), 127.6 (BOM), 126.2 (BOM), 92.8 (BOM), 73.0 (C21), 69.3 (BOM), 63.1 (C1), 53.9 (C2), 40.1 (C20), 32.8 (C16 or C17), 32.6 (C16 or C17), 29.6, 29.6, 29.5, 29.4, 29.2, 29.1, 25.7, 20.8, 19.9 (C3-C13), 14.1 (C22)

HR-MS (ESI-TOF): m/z calcd for C30H50O3Na [M+Na]+: 481.3652, found: 481.3659.

IR (neat): 3402, 2923, 2854 cm-1

[α]D20 +4.29 (c1.05, CHCl3)

Example 3

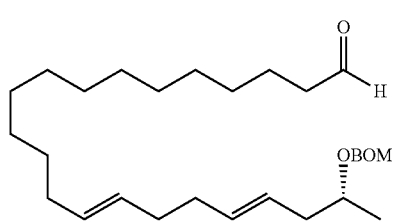

Compound (13)

A mixture of a methylene chloride (15.2 mL) solution of the compound (12) (850 mg, 1.85 mmol) and DMSO (3.8 mL) was cooled to 0° C., and Et3N (2.1 mL, 14.8 mmol) and SO3.Py complex (1.2 g, 7.4 mmol) were added, and then heated to room temperature, and stirred for 2 hours. The reaction system was cooled to 0° C., and saturated aqueous ammonium chloride was added to quench the reaction. The organic phase was fractionated, and then the aqueous phase was washed 3 times with methylene chloride. Fractions of the organic phase were combined together, and washed with saturated brine, and dried over anhydrous sodium sulfate. The solution was filtered, and then concentrated under reduced pressure. The resulting crude product was purified by silica gel column chromatography (hexane/ethyl acetate=30/1) to obtain a compound (13) (698 mg, 82%).

Rf=0.63 (hexane/ethyl acetate=3/1)

1H-NMR (500 MHz, CDCl3): δ9.65 (s, 1H, 1-H), 7.27-7.18 (m, 5H, BOM), 5.43-5.30 (m, 4H, 14-H, 15-H, 18-H, 19-H), 4.70 (m, 2H, BOM), 4.53 (m, 2H, BOM), 3.71 (sx, J=6.3 Hz, 1H, 21-H), 2.31 (m, 2H, 2-H), 2.19 (ddd, J=10.0, 6.9, 6.3 Hz, 1H, 20-H), 2.07 (ddd, J=10.0, 6.9, 6.3 Hz, 1H, 20-H), 1.97 (m, 4H, 13-H, 16-H), 1.88 (m, 2H, 17-H), 1.53 (m, 2H, 3-H), 1.25-1.18 (m, 20H, 4-H to 12H), 1.09 (d, J=6.30 Hz, 3H, 22-H)

13C-NMR (125 MHz, CDCl3): δ202.5 (C1), 137.9 (BOM), 132.5 (C19), 130.7 (C14), 129.4 (C15), 128.2 (BOM), 127.7 (C18), 127.4 (BOM), 126.2 (BOM), 92.6 (BOM), 72.8 (C21), 69.1 (BOM), 43.7 (C2), 39.9 (C20), 32.7 (C16 or C17), 32.5 (C16 or C17), 32.4, 29.5, 29.4, 29.4, 29.3, 29.2, 29.0, 21.9 (C3-C13), 19.8 (C22)

HR-MS (ESI-TOF): m/z calcd for C30H48O3Na [M+Na]+: 479.3496, found: 479.3514.

IR (neat): 2924, 2854, 1727 cm-1

[α]D20 +4.78 (c1.02, CHCl3)

Example 4

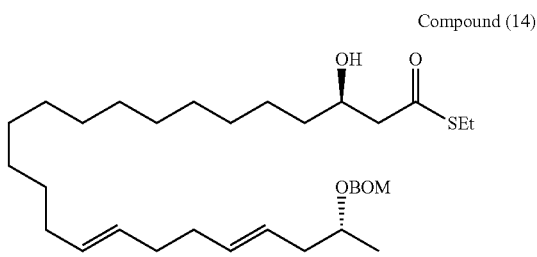

Compound (14)

Sn(OTf)2 (tin triflate) (953 mg, 2.29 mmol) was dried under reduced pressure at 110° C. for 6 hours, and then methylene chloride (21 mL) was added, and a methylene chloride (5 mL) solution of (S)-1-methyl-2-(1-naphthylaminomethyl)pyrrolidine (598 mg, 2.49 mmol) and nBu3SnF (tributyltin fluoride) (708 mg, 2.29 mmol) were quickly added. The reaction system was cooled to −78° C., and then a methylene chloride (2 mL) solution of ketene silylacetal (404 mg, 2.29 mmol) and a methylene chloride (2 mL) solution of the compound (13) (698 mg, 1.53 mmol) were added, and stirred for 12 hours while maintaining the temperature at −78° C. Saturated aqueous sodium hydrogen carbonate was added to quench the reaction, and the mixture was filtered through Celite. The organic phase was fractionated, and then the aqueous phase was extracted 3 times with methylene chloride. Fractions of the organic phase were combined together, and washed with saturated brine, and dried over anhydrous sodium sulfate. The solution was filtered, and then concentrated under reduced pressure. The resulting crude product was purified by silica gel column chromatography (hexane/ethyl acetate=10/1) to obtain a compound (14) (538 mg, 63%, diastereomer ratio=95/5). Note that the above diastereomer ratio was determined by high performance liquid chromatography (column: DAICEL CHIRALPAK AD-H, developing solvent: hexane/2-propanol=50/1 (v/v), flow rate: 1.0 mL/min, wavelength: 254 nm).

Rf=0.3 (hexane/ethyl acetate=5/1)

1H-NMR (500 MHz, CDCl3): δ7.36-7.27, 5.51-5.34, 4.80, 4.61, 4.05, 3.80, 2.90, 2.74, 2.65, 2.28, 2.17, 2.09-2.02, 1.95, 1.55-1.25, 1.17

13C-NMR (125 MHz, CDCl3): δ199.7, 138.0, 132.7, 130.8, 129.4, 128.4, 127.8, 127.6, 126.2, 92.8, 73.0, 69.2, 68.7, 50.6, 40.0, 36.5, 32.8, 32.6, 32.5, 29.6, 29.6, 29.5, 29.5, 29.5, 25.4, 23.3, 19.9, 14.6

HR-MS (ESI-TOF): m/z calcd for C34H56O4SNa [M+Na]+: 583.3792, found: 583.3778.

IR (neat): 2924, 2854, 1727 cm-1

[α]D20 −4.89 (c1.01, CHCl3)

Example 5

Compound (15)

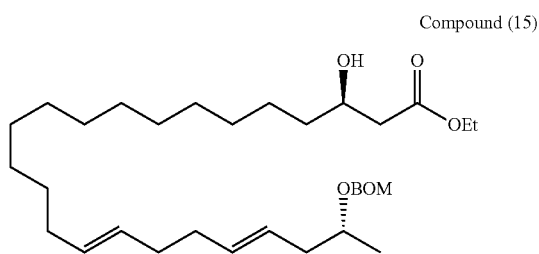

An ethanol (8.4 mL) solution of the compound (14) (470 mg, 0.84 mmol) was cooled to 0° C., and diisopropylethylamine (0.6 mL, 3.35 mmol) and AgOCOCF3 (371 mg, 1.68 mmol) were added sequentially, and then heated to room temperature, and stirred for 3 hours. Water was added to the reaction system to quench the reaction, and filtered through Cerite using ethyl acetate. The organic phase was fractionated, and then the aqueous phase was extracted 3 times with ethyl acetate. Fractions of the organic phase were combined together, and washed with saturated brine, and dried over anhydrous sodium sulfate. The solution was filtered, and then concentrated under reduced pressure. The resulting crude product was purified by silica gel column chromatography (hexane/ethyl acetate=5/1) to obtain a compound (15) (419 mg, 92%).

Rf=0.23 (hexane/ethyl acetate=5/1)

1H-NMR (500 MHz, CDCl3): δ7.35-7.27, 5.52-5.34, 4.80, 4.61, 4.17, 4.00, 3.80, 2.94, 2.51, 2.48, 2.28, 2.15, 2.04, 1.95, 1.63-1.25, 1.17

13C-NMR (125 MHz, CDCl3): δ173.1, 138.0, 132.7, 130.8, 129.5, 128.4, 127.8, 127.6, 126.2, 92.8, 73.0, 69.3, 68.0, 41.3, 40.0, 36.5, 32.8, 32.6, 32.6, 29.6, 29.6, 29.5, 29.2, 25.5, 19.9, 14.6

HR-MS (ESI-TOF): m/z calcd for C34H56O5Na [M+Na]+: 567.4020, found: 567.4000.

IR (neat): 3464, 2924, 2854, 1728 cm-1

[α]D20 −5.16 (c1.00, CHCl3)

Example 6

Compound (16)

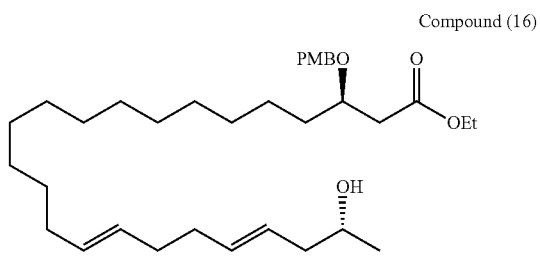

(Step 1) Molecular sieves 4A (1 mg) were heated and dried under reduced pressure, and then allowed to stand for cooling to room temperature, and then a methylene chloride (3.9 mL) solution of the compound (15) (105 mg, 0.19 mmol) was added. After cooled to 0° C., 4-methoxybenzyl-2,2,2-trichloroacetimidate (80 μL, 0.39 mmol) and TsOH.H2O (tosyl acid monohydrate) (13 mg, 77 μmol) were added, and then heated to room temperature, and stirred for 12 hours. Et3N was added to the reaction system to quench the reaction, and filtered through Cerite using methylene chloride, and then concentrated under reduced pressure. Crude purification was performed by silica gel thin layer chromatography (hexane/ethyl acetate=5/1).

(Step 2) The crude product was cooled to 0° C., and a mixed solution (3.8 mL) of THF/12N HCl (5/1) was added, and the reaction system was then heated to room temperature, and stirred for 12 hours. The organic phase was fractionated, and then the aqueous phase was extracted 3 times with diethyl ether. Fractions of the organic phase were combined together, and washed with saturated brine, and dried over anhydrous sodium sulfate. The solution was filtered, and then concentrated under reduced pressure. The resulting crude product was purified by silica gel thin layer chromatography (hexane/ethyl acetate=3/1) to obtain a compound (16) (75 mg, 71%).

Rf=0.3 (hexane/ethyl acetate=3/1)

1H-NMR (500 MHz, CDCl3): δ7.25-7.23, 6.86, 5.58-5.34, 4.46, 4.14, 3.88-3.76, 2.58, 2.44, 2.23-2.17, 2.13-2.04, 1.96, 1.63-1.49, 1.43-1.24, 1.18

13C-NMR (125 MHz, CDCl3): δ172.0, 159.2, 134.3, 131.2, 130.8, 129.4, 126.3, 113.8, 75.9, 71.3, 67.1, 60.5, 56.4, 42.6, 40.1, 34.5, 32.8, 32.7, 32.6, 29.7, 29.7, 29.6, 29.3, 25.3, 22.7, 14.3

HR-MS (ESI-TOF): m/z calcd for C34H56O5Na [M+Na]+: 567.4020, found: 567.4000.

IR (neat): 3464, 2924, 2854, 1728 cm-1

[α]D20 −3.12 (c1.02, CHCl3)

Example 7

Compound (17)

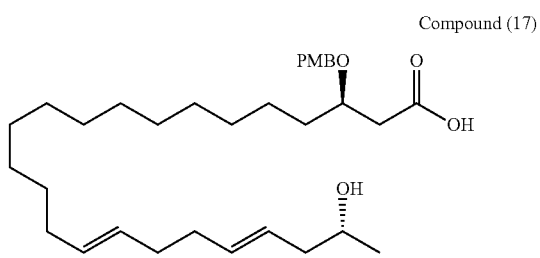

A 40 mM LiOH solution (ethanol/H2O=3/1) (3.4 mL) was added to the compound (16) (75 mg, 1.138 mmol), and stirred at room temperature for 20 hours. The reaction was quenched by adding 1N HCl. The organic phase was fractionated, and then the aqueous phase was extracted 5 times with ethyl acetate. Fractions of the organic phase were combined together, and washed with saturated brine, and dried over anhydrous sodium sulfate. The solution was filtered, and the concentrated under reduced pressure. The resulting crude product was purified by silica gel thin layer chromatography (chloroform/methanol=6/1) to obtain a compound (17) (61 mg, 86%).

Rf=0.59 (chloroform/methanol=6/1)

1H-NMR (500 MHz, CDCl3): δ7.35-7.27, 5.52-5.34, 4.79, 4.61, 4.17, 4.00, 3.80, 2.93, 2.51, 2.48, 2.40, 2.13-2.04, 1.97-1.94, 1.63-1.25, 1.17

13C-NMR (125 MHz, CDCl3): δ174.0, 159.4, 134.3, 131.1, 129.8, 129.6, 129.4, 126.1, 113.9, 75.3, 71.2, 67.1, 60.5, 55.3, 42.5, 39.0, 33.9, 32.7, 32.6, 32.5, 29.7, 29.6, 29.6, 29.5, 29.5, 29.4, 29.1, 25.0, 22.5

HR-MS (ESI-TOF): m/z calcd for C32H52O5Na [M+Na]+: 539.3707, found: 539.3727.

IR (neat): 3464, 2924, 2854, 1728 cm-1

[α]D20 −15.2 (c1.01, CHCl3)

Example 8

Compound (18)

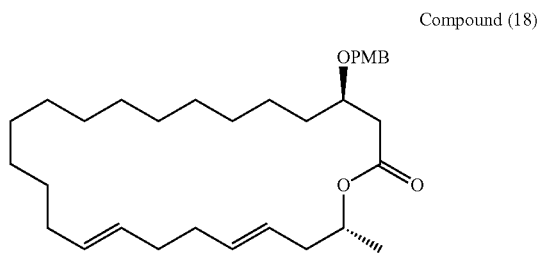

A methylene chloride (4.2 mL) solution of the compound (17) (21 mg, 40.6 μmol) was added dropwise to a methylene chloride (16.8 mL) solution of MNBA (19 mg, 52.8 μmol) and DMAP (4-dimethylaminopyridine) (30 mg, 0.24 mmol) over 12 hours using a syringe pump. After the dropwise addition was ended, rinsing was performed with methylene chloride (1.0 mL), and stirred for 1 hour. The reaction system was cooled to 0° C., and then saturated aqueous sodium hydrogen carbonate was added to quench the reaction. The organic phase was fractionated, and the aqueous phase was then extracted 3 times with methylene chloride. Fractions of the organic phase were combined together, and washed with saturated brine, and dried over anhydrous sodium sulfate. The solution was filtered, and then concentrated under reduced pressure. The resulting crude product was purified by silica gel thin layer chromatography (hexane/ethyl acetate=6/1) to obtain a compound (18) (13 mg, 68%).

Rf=0.4 (hexane/ethyl acetate=6/1)

1H-NMR (500 MHz, CDCl3): δ7.27-7.22, 6.87, 5.44-5.35, 4.91, 4.47, 3.80, 2.65, 2.43, 2.24, 2.04, 1.99, 1.39-1.27, 1.19

13C-NMR (125 MHz, CDCl3): δ170.9 (C1), 159.1 (PMB), 133.5 (C20), 130.8 (C17), 130.6 (C16), 129.8 (PMB), 129.3 (PMB), 125.2 (C21), 113.7 (PMB), 75.5 (C3), 70.7 (C23), 70.6 (PMB), 55.3 (C2), 40.0 (C22), 38.9 (C4), 33.9 (C19), 32.7 (C18), 32.4 (C15), 31.8 (C6), 28.8, 28.6, 28.5, 28.4, 28.4, 28.2, 27.5 (C7-14), 24.4 (C5), 19.4 (C24)

HR-MS (ESI-TOF): m/z calcd for C32H50O4Na [M+Na]+: 521.3601, found: 521.3600.

IR (neat): 2924, 2854, 1728 cm-1

[α]D20 +5.13 (c1.01, CHCl3)

Example 9

Compound (19)

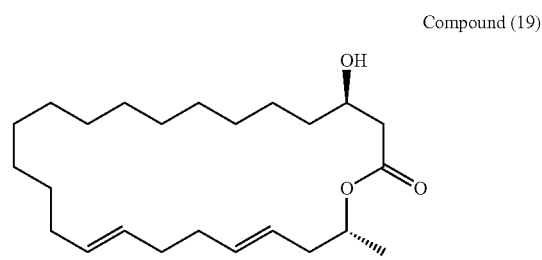 [SMILES: C[C@@H]1C/C=C/CC/C=C/CCCCCCCCCCCC[C@@H](O)CC(=O)O1]

A mixed solution of methylene chloride (1.8 mL) and a phosphate buffer solution (0.18 mL) of the compound (18) (38 mg, 0.10 mmol) was cooled to 0° C., and DDQ (27 mg, 0.12 mmol) was added, and then heated to room temperature, and stirred for 2 hours. The reaction system was cooled to 0° C., and then saturated aqueous sodium hydrogen carbonate was added to quench the reaction. The organic phase was fractionated, and the aqueous phase was then extracted 5 times with methylene chloride. Fractions of the organic phase were combined together, and dried over anhydrous sodium sulfate. The solution was filtered, and then concentrated under reduced pressure. The resulting crude product was purified by silica gel thin layer chromatography (hexane/diethyl ether=2/1) to obtain a compound (19) (31 mg, 82%).

Rf=0.16 (hexane/diethyl ether=2/1)

1H-NMR (500 MHz, CDCl3): δ5.52-5.34, 5.00, 3.94, 2.54-2.39, 2.31-2.17, 2.05, 2.00, 1.34-1.27, 1.25, 1.24

13C-NMR (125 MHz, CDCl3): δ172.2 (C1), 133.7 (C20), 130.7 (C17), 129.8 (C16), 124.9 (C21), 70.8 (C23), 68.2 (C3), 55.3 (C2), 41.4 (C22), 38.9 (C4), 36.1 (C19), 32.9 (C18), 32.5 (C15), 31.9 (C6), 28.6, 28.4, 28.2, 28.2, 28.1, 28.1, 27.9 (C7-14), 24.7 (C5), 19.6 (C24)

HR-MS (ESI-TOF): m/z calcd for C24H42O3Na [M+Na]+: 401.3026, found: 401.3008.

IR (neat): 3410, 2924, 2854, 1728 cm-1

[α]D20 +14.2 (c1.03, CHCl3)

Example 10

Compound (A)

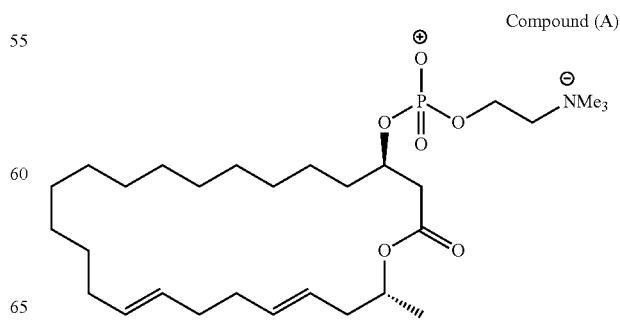

(Step 1) A toluene (0.8 mL) solution of the compound (19) (15 mg, 39.6 mol) was cooled to 0° C., and Et3N (9.4 μL, 67.3 μmol) and 2-chloro-2-oxo-1,3,2-dioxaphospholane (4.7 μL, 51.5 μmol) were added sequentially, and heated to room temperature, and stirred for 3 hours. The amine salt produced from the reaction was filtered by aspiration while washed with anhydrous toluene. The filtrate was concentrated under reduced pressure to obtain a crude product. The crude product was unstable in water and alcohol, and thus directly used in the next reaction without performing purification.

(Step 2) An acetonitrile (0.8 mL) solution of the crude product was cooled to −15° C. using an autoclave as a reaction vessel, and an excess amount of liquid triethylamine was added. The reaction system was sealed, and heated to 70° C., and stirred for 38 hours. The reaction system was returned to room temperature, and the reaction mixture was removed using methanol as a solvent. Purification was performed by amino silica gel column chromatography (chloroform/methanol=6/1) to obtain a compound (A) (9.7 mg, 45%).

Rf=0.27 (methanol)

1H-NMR (500 MHz, CD3OD): δ5.52-5.33 (4H, m, 16, 17-H, 20, 21-H), 4.54 (1H, m, 3-H), 4.27 (2H, br s, 25-H), 3.63 (m, 2H, 26-H), 3.22 (9H, s, 27-H), 2.82 (1H, dd, J=4.0, 14.0 Hz, 2-H), 2.54 (1H, dd, J=8.6, 14.0 Hz, 2-H), 2.31-2.19 (2H, m, 22-H), 2.07 (4H, br s, 18, 19-H), 2.00 (2H, br d, J=4.6 Hz, 15-H), 1.65 (2H, m, 4-H), 1.30 (18H, br s, 5-13H), 1.19 (3H, d, J=6.3 Hz, 24-H)

13C-NMR (125 MHz, CDCl3): δ171.8 (C1), 134.7 (C-20), 131.8 (C16), 126.5 (C21), 74.1 (C3), 72.3 (C23), 67.5 (C26), 60.4 (C25), 54.7 (C27), 41.9 (C2), 40.0 (C22), 36.1 (C4), 33.9 (C19), 33.6 (C18), 32.7 (C15), 30.1 (C6), 29.5 (C14), 29.2, 29.4, 29.6, 29.7, 29.8 (C7-12), 28.5 (C13), 25.4 (C5), 19.7 (C24)

HR-MS (ESI-TOF): m/z calcd for C29H54NO6PNa [M+Na]+: 566.3586, found: 566.3592.

IR (neat): 3432, 2954, 2537, 2090, 1728 cm-1

[α]D20 −10.9 (c0.707, methanol)

Example 11

The compounds (D) to (H) were manufactured by a similar method as used for the compound (A) as described above. The identification data of the compounds (D) to (H) are shown below.

Compound (D)

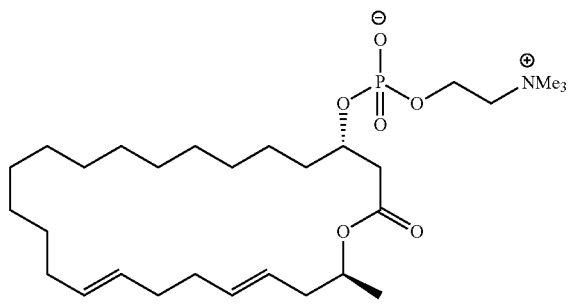

(3S,16E,20E,23S)-(+)-Eushearilide (D)

1H-NMR (500 MHz, CD3OD): δ5.52-5.36 (m, 4H, 16-H, 17-H, 20-H, 21-H), 4.87 (m, 1H, 23-H), 4.54 (m, 1H, 3-H), 4.27 (br s, 2H, 25-H), 3.63 (m, 2H, 26-H), 3.22 (s, 9H, 27-H), 2.82 (dd, J=4.0, 14.0 Hz, 1H, 2-H), 2.54 (dd, J=8.6, 14.0 Hz, 1H, 2-H), 2.31-2.19 (m, 2H, 22-H), 2.07 (br s, 4H, 18-H, 19-H), 2.00 (d, J=4.6 Hz, 2H, 15-H), 1.65 (m, 2H, 4-H), 1.40-1.30 (m, 20H, 5-H to 14-H), 1.19 (d, J=6.3 Hz, 3H, 24-H)

13C-NMR (125 MHz, CD3OD): δ171.7 (C1), 134.7 (C20), 131.8 (C16), 131.2 (C17), 126.5 (C21), 74.1 (d, J=6.0 Hz, C3), 72.3 (C23), 67.5 (C26), 60.4 (d, J=4.8 Hz, C25), 54.7 (C27 (NMe3)), 41.9 (d, J=2.4 Hz, C2), 40.0 (C22), 36.1 (d, J=6.0 Hz, C4), 33.9 (C19), 33.6 (C18), 32.7 (C15), 30.1 (C6), 29.5 (C14), 29.8, 29.7, 29.7, 29.6, 29.4, 29.2 (C7 to C12), 28.5 (C13), 25.4 (C5), 19.7 (C24)

HR-MS (ESI-TOF): m/z calcd for C29H54NO6PNa [M+Na]+566.3586, found 566.3592.

IR (neat): 3432, 2954, 2537, 2090, 1728 cm-1

[α]D25 +11.3 (c0.85, CH3OH)

Compound (E)

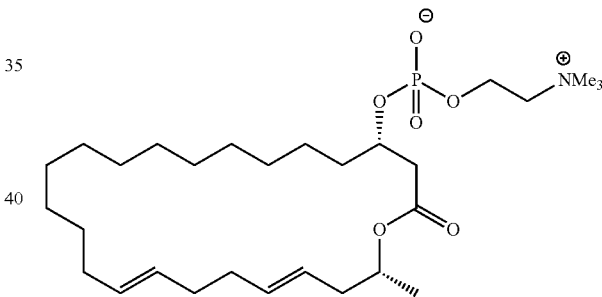

(3S,16E,20E,23R)-(+)-Eushearilide (E)

1H-NMR (500 MHz, CD3OD): δ5.51-5.36 (m, 4H, 16-H, 17-H, 20-H, 21-H), 4.89 (m, 1H, 23-H), 4.53 (m, 1H, 3-H), 4.25 (brs, 2H, 25-H), 3.62 (m, 2H, 26-H), 3.21 (s, 9H, 27-H), 2.81 (dd, J=4.9, 15.2 Hz, 1H, 2-H), 2.51 (dd, J=8.6, 14.3 Hz, 1H, 2-H), 2.28-2.19 (m, 2H, 22-H), 2.06 (br s, 4H, 18-H, 19-H), 1.99 (m, 2H, 15-H), 1.65 (dd, J=6.3 Hz, 2H, 4-H), 1.41-1.29 (m, 20H, 5-H to 14-H), 1.20 (d, J=5.7 Hz, 3H, 24-H)

13C-NMR (125 MHz, CD3OD): δ172.0 (C1), 134.6 (C20), 131.8 (C16), 131.2 (C17), 126.6 (C21), 74.1 (d, J=6.0 Hz, C3), 72.0 (C23), 67.5 (C26), 60.3 (d, J=4.7 Hz, C25), 54.7 (C27), 41.5 (d, J=3.6 Hz, C2), 40.1 (C22), 36.1 (d, J=4.8 Hz, C4), 34.0 (C19), 33.7 (C18), 32.7 (C15), 30.1 (C6), 29.5 (C14), 29.8, 29.8, 29.7, 29.6, 29.3, 29.2 (C7 to C12), 28.4 (C13), 25.4 (C5), 19.8 (C24)

HR-MS (ESI-TOF): m/z calcd for C29H54NO6PNa [M+Na]+566.3581, found 566.3558.
IR (neat): 3410, 2924, 2854, 1720 cm-1
[α]D27 +9.42 (c0.71, CH3OH)

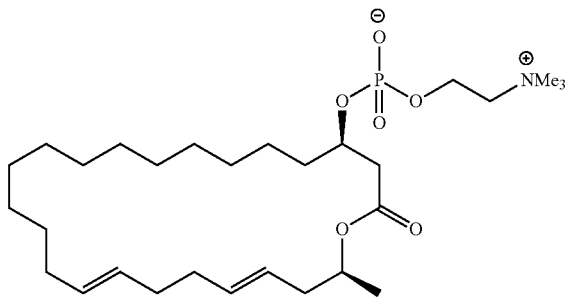

Compound (F)

(3R,16E,20E,23S)-(−)-Eushearilide (F)

1H-NMR (500 MHz, CD3OD): δ5.51-5.36 (m, 4H, 16-H, 17-H, 20-H, 21-H), 4.88 (m, 1H, 23-H), 4.55 (m, 1H, 3-H), 4.26 (brs, 2H, 25-H), 3.63 (m, 2H, 26-H), 3.22 (s, 9H, 27-H), 2.82 (dd, J=4.5, 15.5 Hz, 1H, 2-H), 2.52 (dd, J=8.5, 14.5 Hz, 1H, 2-H), 2.28-2.19 (m, 2H, 22-H), 2.06 (br s, 4H, 18-H, 19-H), 2.00 (d, J=5.5 Hz, 2H, 15-H), 1.65 (m, 2H, 4-H), 1.42-1.30 (m, 20H, 5-H to 14-H), 1.20 (d, J=6.3 Hz, 3H, 24-H)

13C-NMR (125 MHz, CD3OD): δ172.0 (C1), 134.6 (C20), 131.8 (C16), 131.2 (C17), 126.6 (C21), 74.1 (C3), 72.0 (C23), 67.6 (C26), 60.3 (d, J=6.0 Hz, C25), 54.7 (C27), 41.5 (d, J=2.4 Hz, C2), 40.1 (C22), 36.2 (d, J=4.8 Hz, C4), 34.0 (C19), 33.7 (C18), 32.7 (C15), 30.1 (C6), 29.5 (C14), 29.8, 29.8, 29.7, 29.6, 29.3, 29.2 (C7 to C12), 28.4 (C13), 25.4 (C5), 19.8 (C24)

HR-MS (ESI-TOF): m/z calcd for C29H54NO6PNa [M+Na]+566.3581, found 566.3588.
IR (neat): 3433, 2924, 2854, 1720 cm-1
[α]D26 −11.17 (c0.73, CH3OH)

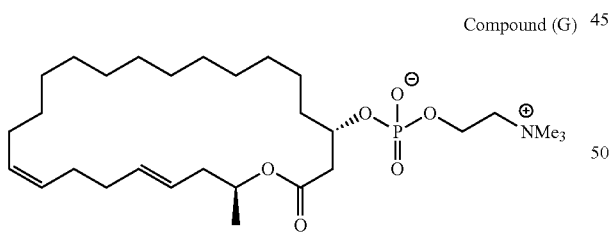

Compound (G)

(3S,16Z,20E,23S)-(+)-Eushearilide (G)

1H-NMR (500 MHz, CD3OD): δ5.54-5.35 (m, 4H, 16-H, 17-H, 20-H, 21-H), 4.87 (m, 1H, 23-H), 4.53 (m, 1H, 3-H), 4.26 (brs, 2H, 25-H), 3.62 (m, 2H, 26-H), 3.21 (s, 9H, 27-H), 2.82 (dd, J=4.5, 14.5 Hz, 1H, 2-H), 2.53 (dd, J=8.0, 14.5 Hz, 1H, 2-H), 2.29-2.19 (m, 2H, 22-H), 2.08-2.03 (m, 6H, 15-H, 18-H, 19-H), 1.64 (m, 2H, 4-H), 1.43-1.30 (m, 20H, 5-H to 14-H), 1.20 (d, J=6.3 Hz, 3H, 24-H)

13C-NMR (125 MHz, CD3OD): δ171.8 (C1), 134.8 (C20), 131.3 (C16), 130.3 (C17), 126.4 (C21), 74.1 (C3), 72.2 (C23), 67.5 (d, J=4.8 Hz, C26), 60.3 (C25), 54.7 (C27), 42.0 (C2), 40.1 (C22), 36.0 (C4), 33.8 (C19), 29.8 (C18), 29.8 (C15), 30.0 (C6), 27.5 (C14), 29.9, 29.8, 29.7, 29.7, 29.4, 29.2 (C7 to C12), 28.4 (C13), 25.4 (C5), 19.7 (C24)

HR-MS (ESI-TOF): m/z calcd for C29H54NO6PNa [M+Na]+566.3581, found 566.3590.
IR (neat): 3433, 2924, 2862, 1720 cm-1
[α]D29 +5.91 (c0.80, CH3OH)

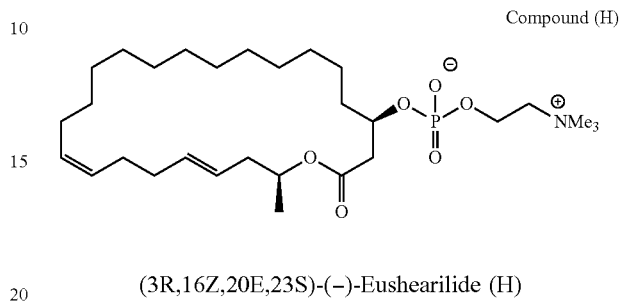

Compound (H)

(3R,16Z,20E,23S)-(−)-Eushearilide (H)

1H-NMR (500 MHz, CD3OD): δ5.54-5.32 (m, 4H, 16-H, 17-H, 20-H, 21-H), 4.88 (m, 1H, 23-H), 4.54 (m, 1H, 3-H), 4.26 (brs, 2H, 25-H), 3.63 (m, 2H, 26-H), 3.22 (s, 9H, 27-H), 2.83 (dd, J=3.4, 14.9 Hz, 1H, 2-H), 2.51 (dd, J=8.6, 14.9 Hz, 1H, 2-H), 2.28-2.19 (m, 2H, 22-H), 2.11-2.03 (m, 6H, 15-H, 18-H, 19-H), 1.65 (m, 2H, 4-H), 1.43-1.31 (m, 20H, 5-H to 13-H), 1.20 (d, J=6.3 Hz, 3H, 24-H)

13C-NMR (125 MHz, CD3OD): δ172.0 (C1), 134.7 (C20), 131.3 (C16), 130.2 (C17), 126.5 (C21), 74.1 (d, J=6.0 Hz, C3), 72.1 (C23), 67.6 (C26), 60.3 (d, J=4.9 Hz, C25), 54.7 (C27), 41.6 (d, J=3.6 Hz, C2), 40.2 (C22), 36.1 (d, J=4.8 Hz, C4), 33.9 (C19), 29.8 (C18), 29.7 (C15), 30.0 (C6), 27.5 (C14), 29.9, 29.7, 29.7, 29.6, 29.4, 29.2 (C7 to C12), 28.4 (C13), 25.4 (C5), 19.8 (C24)

HR-MS (ESI-TOF): m/z calcd for C29H54NO6PNa [M+Na]+566.3581, found 566.3560.
IR (neat): 3448, 2924, 2862, 1728 cm-1
[α]D27 −10.53 (c0.81, CH3OH)

Example 12

An intermediate for manufacturing the compound (E) was synthesized according to the following scheme.

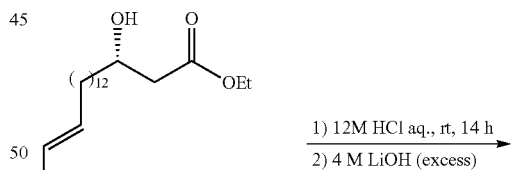

Compound (20)

1) 12M HCl aq., rt, 14 h
2) 4 M LiOH (excess)
rt, 24 h

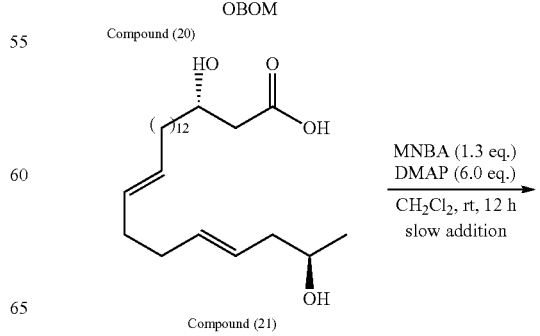

Compound (21)

MNBA (1.3 eq.)
DMAP (6.0 eq.)

CH2Cl2, rt, 12 h
slow addition

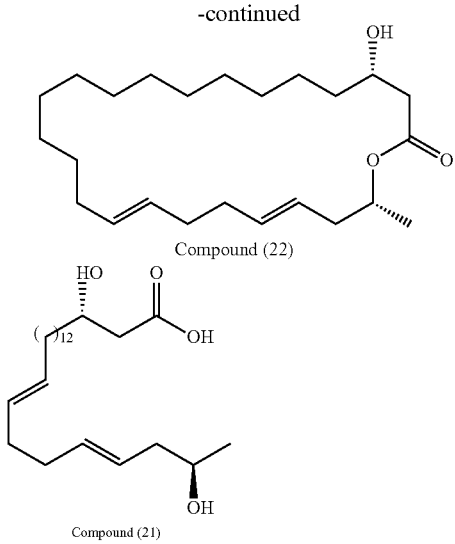

Compound (22)

Compound (21)

An ethanol solution (HCl/EtOH=1/5, 5.9 mL) of 12 M hydrochloric acid was added to the compound (20) (161 mg, 0.30 mmol), and stirred at room temperature for 14 hours. The reaction solution was cooled to 0° C., and 4 M aqueous LiOH was added to neutralize hydrochloric acid. Next, 1 mL of water was added to dilute the solution, and then 4 M aqueous LiOH (0.15 mL, 2 eq.) was added, and stirred at room temperature for 24 hours. After confirming the completion of the reaction by TLC, 1 M hydrochloric acid was added (pH=2 to 3), and extraction was performed 5 times with ethyl acetate. The resulting organic layer was purified again by extraction procedures. That is, 10% aqueous sodium hydroxide was added (pH=9 to 11) to perform liquid partitioning, and then the aqueous layer was fractionated. To this aqueous phase, added was 1 M hydrochloric acid (pH=2 to 3). Extraction was performed 5 times with ethyl acetate. The resulting final organic phase was washed with saturated brine, and dried over anhydrous sodium sulfate, and concentrated under reduced pressure to obtain a compound (21) of interest (111 mg, 95%).

1H-NMR (500 MHz, CDCl3): δ5.55-5.33 (m, 4H, 16-H, 17-H, 20-H, 21-H), 4.04-3.99 (m, 1H, 3-H), 3.79 (sx, J=6.1 Hz, 23-H), 2.55 (dd, J=2.6, 16.3 Hz, 1H, 2-H), 2.45 (dd, J=9.2, 16.6 Hz, 1H, 2-H), 2.22-2.17 (m, 1H, 22-H), 2.11-2.04 (m, 5H, 22-H, 18-H, 19-H), 1.96 (q, J=6.5 Hz, 2H, 15-H), 1.57-1.43 (m, 4H, 4-H, 5-H), 1.31-1.25 (18H, m, 6-H to 14-H), 1.18 (d, J=6.3 Hz, 3H, 24-H)

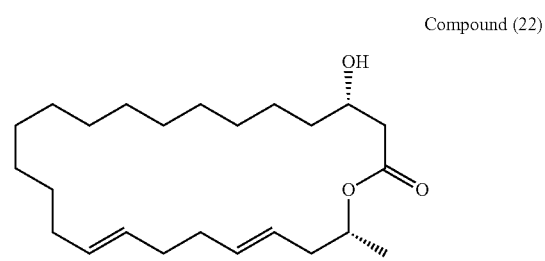 [SMILES: C[C@@H]1C/C=C/CC/C=C/CCCCCCCCCCCC[C@H](O)CC(=O)O1]

Compound (22)

A methylene chloride (5.6 mL) solution of the compound (21) (21.5 mg, 0.05 mmol) was added dropwise to a methylene chloride (22.4 mL) solution of MNBA (24 mg, 0.07 mol) and DMAP (40 mg, 0.33 mmol) over 12 hours using a syringe pump. After the dropwise addition was ended, rinsing was performed with methylene chloride (1.0 mL), and stirred for 1 hour. The reaction system was cooled to 0° C., and then saturated aqueous sodium hydrogen carbonate was added to quench the reaction. The organic phase was fractionated, and the aqueous phase was then extracted 3 times with methylene chloride. Fractions of the organic phase were combined together, and washed with saturated brine, and dried over anhydrous sodium sulfate. The solution was filtered, and then concentrated under reduced pressure. The resulting crude product was purified by silica gel column chromatography (hexane/ethyl acetate=5/1) to obtain a compound (22) (17.1 mg, 83%).

1H-NMR (500 MHz, CDCl3): δ5.51-5.33 (m, 4H, 16-H, 17-H, 20-H, 21-H), 5.00 (sx, J=6.3 Hz, 1H, 3-H), 3.96 (m, 1H, 23-H), 2.83 (d, J=4.0 Hz, 1H, OH), 2.48 (dd, J=3.4, 16.0 Hz, 1H, 2-H), 2.38 (dd, J=8.3, 15.8 Hz, 1H, 2-H), 2.31-2.18 (m, 2H, 22-H), 2.04 (br s, 4H, 18-H, 19-H), 1.99 (dd, J=6.6, 11.2 Hz, 2H, 15-H), 1.58-1.27 (m, 22H, 4-H to 14-H), 1.24 (d, J=6.3 Hz, 3H, 24-H)

Example of Pharmacological Test 1

Antimicrobial activities of the compounds synthesized according to the manufacturing method of the present invention were evaluated as follows. The structural formulae of the compounds (A) to (C) used for pharmacological tests are shown below.

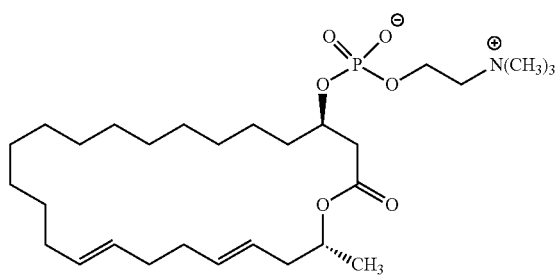

(A)

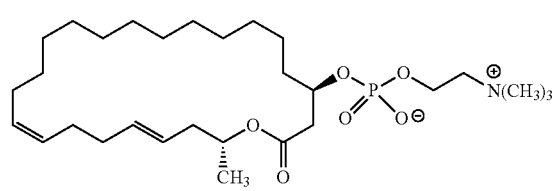

(B)

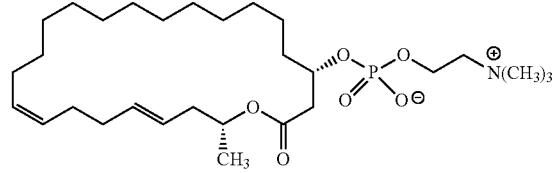

(C)

(1) Test Microorganisms

The followings were used as test microorganisms: *Staphylococcus aureus* NBRC 12732, *Aspergillus niger* NBRC 105649, and *Trichophyton mentagrophytes* NBRC 5466.

(2) Test Method

Measurements were performed in accordance with the disk method as defined by CLSI (Clinical and Laboratory Standards Institute).

(3) Preparation of Test-Bacterium Liquid

A cryopreserved strain was applied onto a test-bacterium preculture medium, and precultured under predetermined conditions. A grown colony was suspended in a test-bacterium culture medium, and cultured under predetermined conditions, and then added to a test-bacterium preparation liquid to adjust the number of cells to about 107-8 CFU/mL. Further, the prepared test-bacterium liquid was subjected to 10-times serial dilution, and cultured under predetermined conditions, and the number of cells was then counted. The preparation of test-bacterium liquids and culture conditions are shown in Table 1.

TABLE 1

Test-bacterium preparation liquid, culture medium, and culture condition

| Test bacterium | Test-bacterium culture medium | Test-bacterium preparation liquid | Susceptibility measurement medium | Culture conditions |
|---|---|---|---|---|
| Staphylococcus aureus | Tryptic Soy Agar (Difco) | Physiological saline | Mueller-Hinton II agar medium (BBL) | 36 ± 1° C., 18 to 24 hours |
| Aspergillus niger Trichophyton mentagrophytes | Potato dextrose agar medium (Nissui Pharmaceutical Co., Ltd.) | 0.005% aerosol OT-containing physiological saline | Glucose Peptone agar medium (Daigo) | 27 ± 1° C., one week |

(4) Preparation of Test-Substance Dilution Series

Each compound was dissolved in methanol to 1,000 μg/mL, which was used as a sample stock solution. Otsuka distilled water in an amount of 0.75 mL was added to 0.75 mL of the sample stock solution to give a volume of 500 μg/mL. This two-fold dilution was repeated in a similar way. A total of 10 test-substance dilution series was prepared so that the concentrations of the test substance were each 1000, 500, 250, 125, 63, 31, 16, 8, 4, and 2 μg/mL.

(5) MIC Measurements

A test-bacterium liquid was uniformly spread over a corresponding sensitivity measurement agar medium in a square petri dish using a swab, and disks were placed on the medium. At this time, the distance between disks was set to 24 mm or more. A test-substance diluted liquid in an amount of 50 μL was dropped on a disk. The amount of a test substance per disk was 50, 25, 12.5, 6.3, 3.1, 1.6, 0.8, 0.4, 0.2, or 0.1 μg. Each sensitivity measurement agar medium was cultured under conditions shown in Table 1 above, and the diameter of an inhibition zone where bacterial growth was not observed was measured in mm with calipers. As control, methanol was dropped on a disk instead of a test substance.

(6) Test Results

Test results are shown in Table 2.

TABLE 2

MIC measurement results of Compounds A to C

| Identity of test bacterium | Test conditions | MIC concentration (μg/disk) | Inhibition zone (mm) |
|---|---|---|---|
| Staphylococcus aureus NBRC 12732 | Control | | 0 |
| | Compound A | 50 | 2 |
| | Compound B | 50 | 2.2 |
| | Compound C | 50 | 1.5 |
| Aspergillus niger NBRC 105649 | Control | | 0 |
| | Compound A | 50 | 3.7 |
| | Compound B | 50 | 3.7 |
| | Compound C | 50 | 1 |

TABLE 2-continued

MIC measurement results of Compounds A to C

| Identity of test bacterium | Test conditions | MIC concentration (μg/disk) | Inhibition zone (mm) |
|---|---|---|---|
| Trichophyton mentagrophytes NBRC 5466 | Control | | 0 |
| | Compound A | 25 | 2.5 |
| | Compound B | 12.5 | 3.9 |
| | Compound C | 12.5 | 5.1 |

Inhibition zone: the mean value of the longest and shortest lengths of an area where bacterial growth is not observed.

The MIC value and the size of an inhibition zone were determined for each of the compounds (A) to (C). For *Staphylococcus aureus*, the sizes were 2 mm, 2.2 mm, and 1.5 mm for 50 μg/disk of the compound (A), the compound (B), and the compound (C), respectively. For *Aspergillus niger*, the sizes were 3.7 mm, 3.7 mm, and 1 mm for 50 μg/disk of the compound (A), the compound (B), and the compound (C), respectively. For *Trichophyton mentagrophytes*, the sizes were 2.5 mm, 3.9 mm, and 5.1 mm for 25 μg/disk of the compound (A), 12.5 μg/disk of the compound (B), and 12.5 μg/disk of the compound (C), respectively. These results clearly indicate that the compounds (A) to (C) are all have an antimicrobial activity.

Example of Pharmacological Test 2

Antimicrobial activities of the compounds (the compounds (D) to (H)) synthesized according to the manufacturing method of the present invention were evaluated as follows. The structural formulae of the compounds (D) to (H) used for pharmacological tests are shown below.

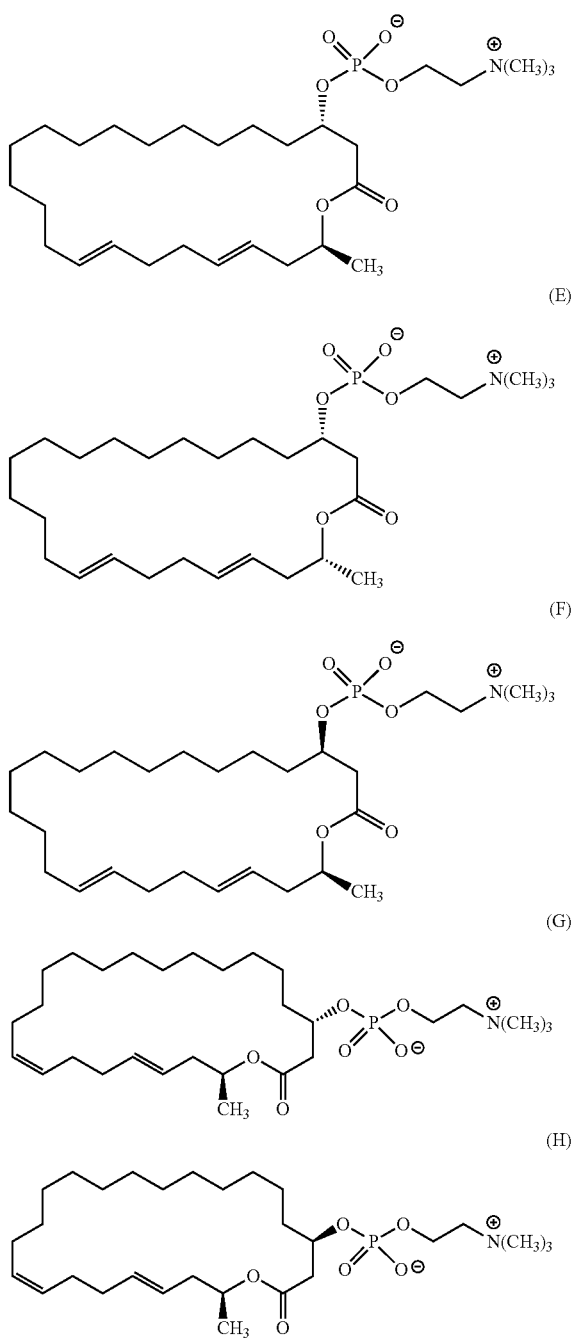

(1) Test Microorganisms

The followings were used as test microorganisms: *Staphylococcus aureus* (MRSA) IID 1677, *Staphylococcus aureus* (MRSA) ATCC 43300, *Enterococcus faecalis* (VRE) ATCC 51575, and *Enterococcus faecalis* ATCC 29212.

(2) Test Method

Measurements were performed in accordance with the disk method as defined by CLSI (Clinical and Laboratory Standards Institute).

(3) Preparation of Test-Bacterium Liquid

A cryopreserved strain was applied onto a test-bacterium culture medium, and precultured under predetermined conditions (Table 3). A grown colony was again precultured (Table 3), and then suspended in a test-bacterium preparation liquid, and filtered through absorbent cotton. The number of cells was then adjusted to about 107-8 CFU/mL. This was used for the tests. Further, the prepared test-bacterium liquid was subjected to 10-times serial dilution, and cultured under predetermined conditions (Table 4), and the number of cells was then counted.

TABLE 3

Preculture conditions and test-bacterium preparation liquids

| Test-bacterium culture medium (Medium for counting the number of cells) | Preculture conditions | Test-bacterium preparation liquid |
|---|---|---|
| Tryptic soy agar (Difco) | 35 ± 1° C., 24 ± 2 h | Sterilized physiological saline |

TABLE 4

Post-culture conditions

| | Post-culture conditions | |
|---|---|---|
| | Medium used | |
| Susceptibility measurement | Mueller-Hinton II agar medium (BBL) | 35 ± 1° C., 24 h |
| Counting of the number of cells | Tryptic soy agar (Difco) | 35 ± 1° C., 48 ± 3 h |

(4) Preparation of Test-Substance Dilution Series

Each of the compounds according to the present invention was dissolved in methanol (Wako Pure Chemical Industries, Ltd., Special grade, Content: 99.8%) to 1000 g/mL. This was used as a sample stock solution. Otsuka distilled water in an amount of 0.8 mL was added to 0.8 mL of the sample stock solution such that the concentration of each of the compounds according to the present invention was 500 µg/mL. This two-fold dilution was repeated in a similar way. A total of 10 test-substance dilution series were prepared so that the concentrations of the test substance were each 1000, 500, 250, 125, 63, 31, 16, 8, 4, and 2 µg/mL.

(5) MIC measurements

A test-bacterium liquid was uniformly spread over a sensitivity measurement agar medium in a square petri dish (230×80×14.5 mm, Eiken Chemical Co., Ltd.) using a swab, and φ8-mm thick disks (for antibiotics assay, Advantec Co., Ltd.) were placed on the medium. At this time, the distance between disks was set to 24 mm or more. A test-substance diluted liquid in an amount of 50 µL was dropped on a disk. The amount of a test substance per disk was 50, 25, 12.5, 6.3, 3.1, 1.6, 0.8, 0.4, 0.2, or 0.1 µg. A sensitivity measurement agar medium was cultured under predetermined conditions (Table 4), and the width of an inhibition zone where bacterial growth was not observed was measured in mm with calipers. As control, methanol was dropped on a disk instead of a test substance.

(6) Test Results

Test results are shown in Table 5.

TABLE 5

MIC measurement results of Compounds D to H

| Identity of test bacterium | Drug candidate | MIC*[1] (μg/disk) | Inhibition zone*[2] (mm) |
|---|---|---|---|
| Staphylococcus aureus | Compound D | 50 | 1.4 |
| (MRSA) IID1677 | Compound E | 50 | 2.2 |
| (Concentration of bacterial | Compound F | 50 | 3.1 |
| liquid: 7.3 × 10⁷ CFU/mL) | Compound G | 50 | 2.3 |
|  | Compound H | 50 | 3.0 |
| Staphylococcus aureus | Compound D | 50 | 3.0 |
| (MRSA) ATCC43300 | Compound E | 50 | 3.3 |
| (Concentration of bacterial | Compound F | 50 | 2.4 |
| liquid: 1.0 × 10⁸ CFU/mL) | Compound G | 50 | 0.9 |
|  | Compound H | 50 | 2.7 |
| Enterococcus faecalis | Compound D | 50 | 4.7 |
| (VRE) ATCC51575 | Compound E | 50 | 6.9 |
| (Concentration of bacterial | Compound F | 50 | 5.8 |
| liquid: 1.9 × 10⁸ CFU/mL) | Compound G | 50 | 6.7 |
|  | Compound H | 50 | 5.5 |
| Enterococcus faecalis | Compound D | 25 | 2.2 |
| ATCC29212 | Compound E | >50 | 0.0 |
| (Concentration of bacterial | Compound F | 50 | 7.7 |
| liquid: 9.6 × 10⁷ CFU/mL) | Compound G | 50 | 8.4 |
|  | Compound H | 50 | 3.3 |

*[1]The amount of a test substance in 50 μL of a test-substance diluted liquid (μg/mL) dropped on a disk.
*[2]The mean value of the longest and shortest lengths of an area where bacterial growth is not observed.

These results clearly indicate that the compounds (D) to (H) all have an antimicrobial activity against methicillin-resistant *Staphylococcus aureus* (MRSA) and vancomycin-resistant *Enterococcus* (VRE), which are resistant bacteria. The vancomycin-resistant gene is known to be horizontally-transmissible among bacterial species (W. C. Noble et al., FEMS Microbiology Letters 1992, Vol. 93, p. 195-198; Elena Ramos-Trujillo et al., Int Microbiol, 2003, No. 6, p. 113-115), and thus the mechanism of acquired drug resistance will be shared. Therefore, the compounds (D) to (H) are all likely to have an antimicrobial activity against vancomycin-resistant *Staphylococcus aureus* (VRSA).

Moreover, the results clearly indicate that the compounds (D) and (F) to (H) also have an antimicrobial activity against bacteria other than resistant bacteria.

The invention claimed is:

1. The method of manufacturing eushearilides represented by the formula (I), the method comprising the following steps 1 to 10:

Step 1: a step of coupling a compound represented by the formula (I-1):

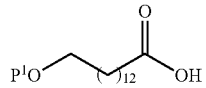

(I-1)

wherein $P^1$ represents a protecting group, with a compound represented by the formula (I-2):

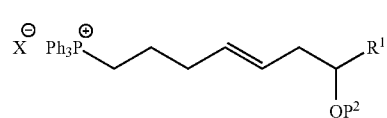

(I-2)

wherein $R^1$ represents a hydrogen atom or an optionally substituted hydrocarbon group, wherein the hydrocarbon group is an alkyl group having 1 to 8 carbon atoms, an alkenyl group having 2 to 8 carbon atoms, an alkynyl group having 2 to 8 carbon atoms, or an aryl group having 6 to 18 carbon atoms, and wherein the substituent is a hydroxy group, an alkoxycarbonyl group having 1 to 8 carbon atoms in the alkoxy moiety, an amino group, a nitro group, a cyano group, an alkoxy group having 1 to 8 carbon atoms, a carboxy group, or a phosphate group, and $P^2$ represents a protecting group, and X represents a halogen atom, in the presence of a base to obtain a compound represented by the formula (I-3):

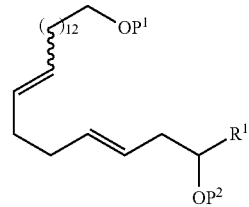

(I-3)

wherein $R^1$, $P^1$, and $P^2$ are as defined above;

Step 2: a step of deprotecting the compound represented by the formula (I-3) to obtain a compound represented by the formula (I-4):

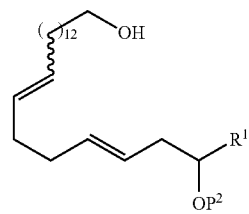

(I-4)

wherein $R^1$ and $P^2$ are as defined above;

Step 3: a step of oxidizing the compound represented by the formula (I-4) to obtain a compound represented by the formula (I-5):

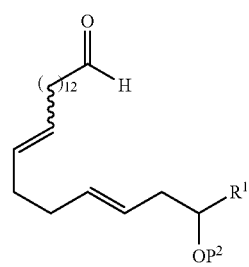

(I-5)

wherein $R^1$ and $P^2$ are as defined above;

Step 4: a step of subjecting the compound represented by the formula (I-5) to the aldol reaction to obtain a compound represented by the formula (I-6):

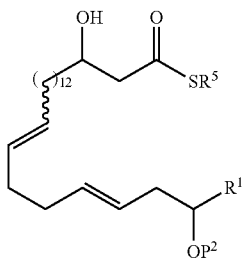
(I-6)

wherein $R^5$ represents a hydrocarbon group, wherein the hydrocarbon group is an alkyl group having 1 to 8 carbon atoms, an alkenyl group having 2 to 8 carbon atoms, an alkynyl group having 2 to 8 carbon atoms, or an aryl group having 6 to 18 carbon atoms, and $R^1$ and $P^2$ are as defined above;

Step 5: a step of transesterifying the compound represented by the formula (I-6) to obtain a compound represented by the formula (I-7):

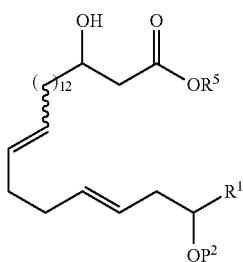
(I-7)

wherein $R^1$, $R^5$, and $P^2$ are as defined above;

Step 6: a step of protecting, deprotecting the compound represented by the formula (I-7) to obtain a compound represented by the formula (I-8):

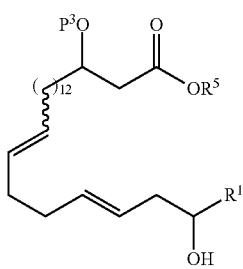
(I-8)

wherein $P^3$ represents a protecting group, and $R^1$ and $R^5$ are as defined above;

Step 7: a step of hydrolyzing the compound represented by the formula (I-8) to obtain a compound represented by the formula (I-9):

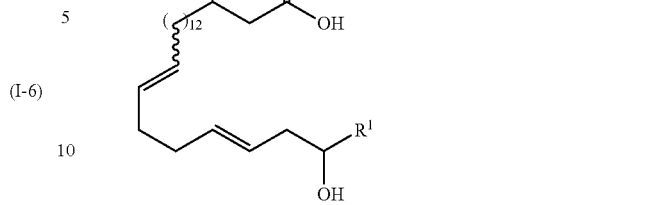
(I-9)

wherein $R^1$ and $P^3$ are as defined above;

Step 8: a step of cyclizing the compound represented by the formula (I-9) to obtain a compound represented by the formula (I-10);

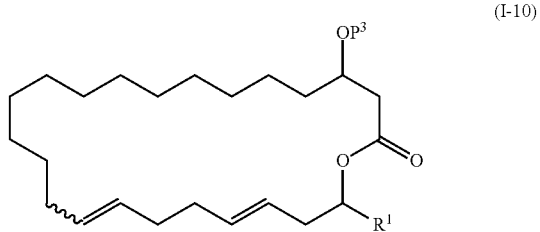
(I-10)

wherein $R^1$ and $P^3$ are as defined above;

Step 9: a step of deprotecting the compound represented by the formula (I-10) to obtain a compound represented by the formula (I-11):

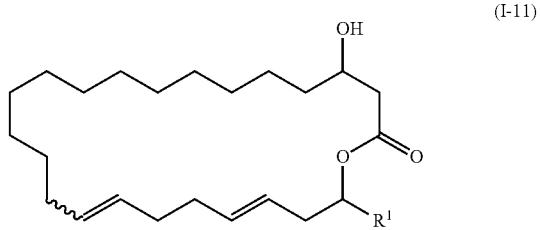
(I-11)

wherein $R^1$ is as defined above;

Step 10: a step of allowing the compound represented by the formula (I-11) to react with a phosphorus compound, and then with an amine $R^2R^3R^4N$ to obtain a compound represented by the formula (I):

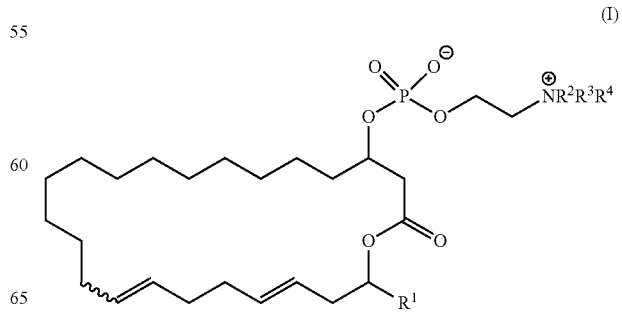
(I)

wherein R¹ is as defined above, and R², R³, and R⁴ independently represent a hydrogen atom or an optionally substituted hydrocarbon group, wherein the hydrocarbon group is an alkyl group having 1 to 8 carbon atoms, an alkenyl group having 2 to 8 carbon atoms, an alkynyl group having 2 to 8 carbon atoms, or an aryl group having 6 to 18 carbon atoms, and wherein the substituent is a hydroxy group, an alkoxycarbonyl group having 1 to 8 carbon atoms in the alkoxy moiety, an amino group, a nitro group, a cyano group, an alkoxy group having 1 to 8 carbon atoms, a carboxy group, or a phosphate group.

2. A method of manufacturing eushearilides represented by the formula (Ia), comprising: allowing a compound represented by the formula (Ia-11):

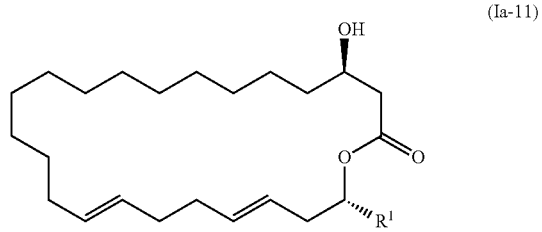

to react with a phosphorus compound, and then with an amine R²R³R⁴N to obtain the eushearilides represented by the formula (Ia):

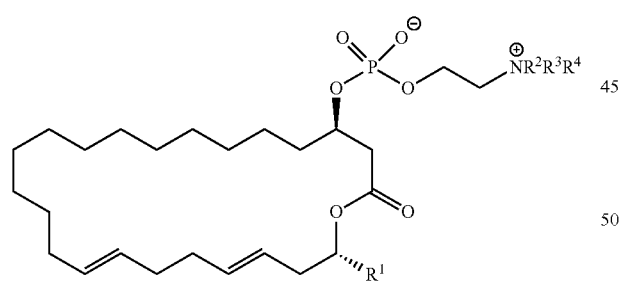

wherein R¹, R², R³, and R⁴ independently represent a hydrogen atom or an optionally substituted hydrocarbon group, wherein the hydrocarbon group is an alkyl group having 1 to 8 carbon atoms, an alkenyl group having 2 to 8 carbon atoms, an alkynyl group having 2 to 8 carbon atoms, or an aryl group having 6 to 18 carbon atoms, and wherein the substituent is a hydroxy group, an alkoxycarbonyl group having 1 to 8 carbon atoms in the alkoxy moiety, an amino group, a nitro group, a cyano group, an alkoxy group having 1 to 8 carbon atoms, a carboxy group, or a phosphate group.

3. The method according to claim 2, wherein the compound represented by the formula (Ia-11) is obtained by:

a step of allowing a compound represented by the formula (Ia-9):

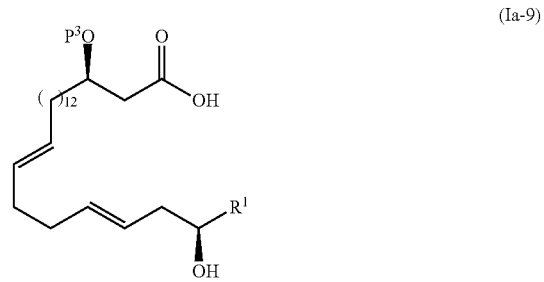

wherein R¹ is as defined above, and P³ represents a protecting group, to react with 2-methyl-6-nitrobenzoic anhydride to obtain a compound represented by the formula (Ia-10):

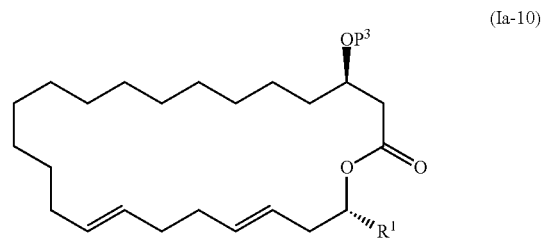

wherein R¹ and P³ are as defined above; and a step of deprotecting the compound represented by the formula (Ia-10).

4. The method according to claim 3, wherein the compound represented by the formula (Ia-9) is obtained by:

a step of coupling the compound represented by the formula (I-1):

wherein P¹ represents a protecting group, with a compound represented by the formula (Ia-2):

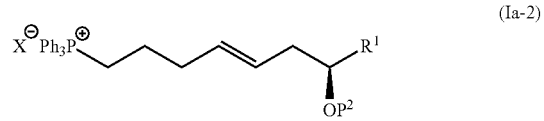

wherein R¹ is as defined above, and P² represents a protecting group, and X represents a halogen atom, in the presence of a base to obtain a compound represented by the formula (Ia-3):

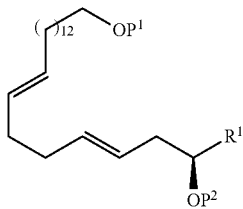
(Ia-3)

wherein $R^1$, $P^1$, and $P^2$ are as defined above;
a step of deprotecting the compound represented by the formula (Ia-3) to obtain a compound represented by the formula (Ia-4):

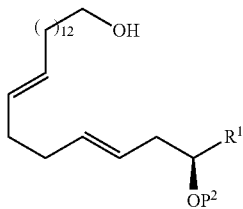
(Ia-4)

wherein $R^1$ and $P^2$ are as defined above;
a step of oxidizing the compound represented by the formula (Ia-4) to obtain a compound represented by the formula (Ia-5):

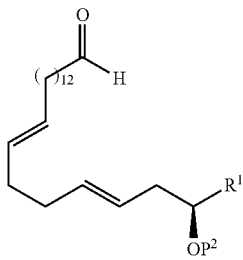
(Ia-5)

wherein $R^1$ and $P^2$ are as defined above;
a step of subjecting the compound represented by the formula (Ia-5) to the aldol reaction to obtain a compound represented by the formula (Ia-6):

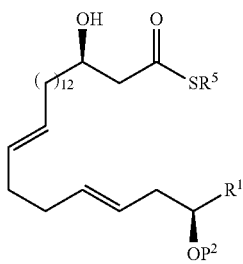
(Ia-6)

wherein $R^5$ represents a hydrocarbon group, wherein the hydrocarbon group is an alkyl group having 1 to 8 carbon atoms, an alkenyl group having 2 to 8 carbon atoms, an alkynyl group having 2 to 8 carbon atoms, or an aryl group having 6 to 18 carbon atoms, and $R^1$ and $P^2$ are as defined above;

a step of transesterifying the compound represented by the formula (Ia-6) to obtain a compound represented by the formula (Ia-7):

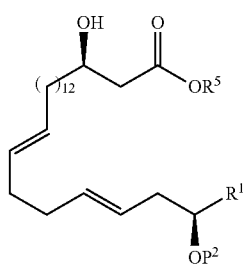
(Ia-7)

wherein $R^1$, $R^5$, and $P^2$ are as defined above;
a step of protecting, deprotecting the compound represented by the formula (Ia-7) to obtain a compound represented by the formula (Ia-8):

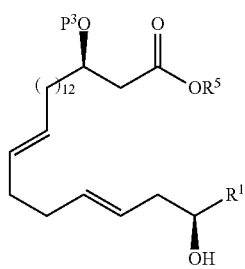
(Ia-8)

wherein $R^1$, $R^5$, and $P^3$ are as defined above; and
a step of hydrolyzing the compound represented by the formula (Ia-8).

5. The method according to claim 2, wherein the eushearilides represented by the formula (Ia) is a compound represented by the formula (A):

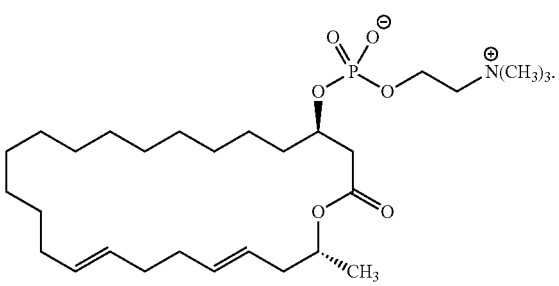
(A)

6. A method of manufacturing eushearilides represented by the formula (I), comprising a step of deprotecting and then cyclizing a compound represented by the formula (I-7):

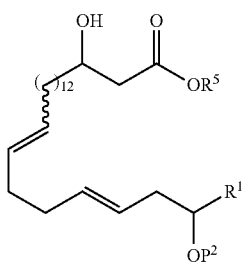
(I-7)

wherein $R^1$ represents a hydrogen atom or an optionally substituted hydrocarbon group, wherein the hydrocarbon group is an alkyl group having 1 to 8 carbon atoms, an alkenyl group having 2 to 8 carbon atoms, an alkynyl group having 2 to 8 carbon atoms, or an aryl group having 6 to 18 carbon atoms, and wherein the substituent is a hydroxy group, an alkoxycarbonyl group having 1 to 8 carbon atoms in the alkoxy moiety, an amino group, a nitro group, a cyano group, an alkoxy group having 1 to 8 carbon atoms, a carboxy group, or a phosphate group, and $P^2$ represents a protecting group, and $R^5$ represents a hydrocarbon group, wherein the hydrocarbon group is an alkyl group having 1 to 8 carbon atoms an alkenyl group having 2 to 8 carbon atoms, an alkynyl group having 2 to 8 carbon atoms, or an aryl group having 6 to 18 carbon atoms, to obtain the eushearilides represented by the formula (I):

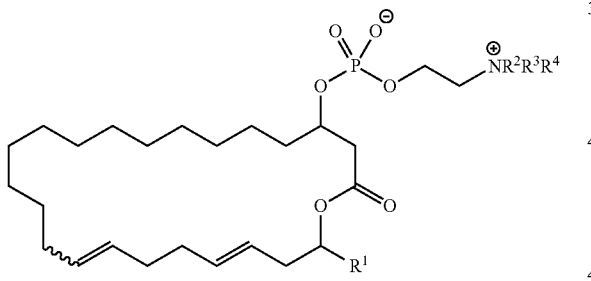
(I)

wherein $R^1$ is as defined above, and $R^2$, $R^3$, and $R^4$ independently represent a hydrogen atom or an optionally substituted hydrocarbon group, wherein the hydrocarbon group is an alkyl group having 1 to 8 carbon atoms, an alkenyl group having 2 to 8 carbon atoms, an alkynyl group having 2 to 8 carbon atoms, or an aryl group having 6 to 18 carbon atoms, and wherein the substituent is a hydroxy group, an alkoxycarbonyl group having 1 to 8 carbon atoms in the alkoxy moiety, an amino group, a nitro group, a cyano group, an alkoxy group having 1 to 8 carbon atoms, a carboxy group, or a phosphate group.

7. The method according to claim 6, comprising:

a step of deprotecting the compound represented by the formula (I-7):

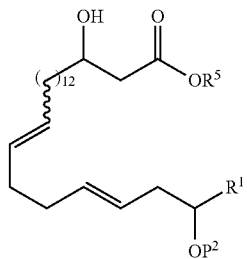
(I-7)

wherein $R^1$ and $P^2$ are as defined above, and $R^5$ represents a hydrocarbon group, wherein the hydrocarbon group is an alkyl group having 1 to 8 carbon atoms, an alkenyl group having 2 to 8 carbon atoms, an alkynyl group having 2 to 8 carbon atoms, or an aryl group having 6 to 18 carbon atoms, to obtain a compound represented by the formula (I-12):

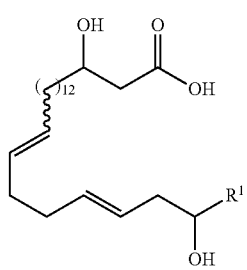
(I-12)

wherein $R^1$ is as defined above; and a step of cyclizing the compound represented by the formula (I-12) to obtain a compound represented by the formula (I-11):

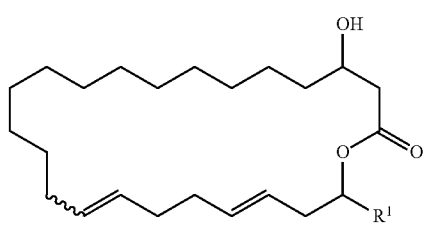
(I-11)

wherein $R^1$ is as defined above.

* * * * *